(12) United States Patent
Solomon et al.

(10) Patent No.: US 11,437,148 B2
(45) Date of Patent: Sep. 6, 2022

(54) SYSTEM FOR PREDICTING TREATMENT OUTCOMES BASED UPON GENETIC IMPUTATION

(71) Applicant: Immunai Inc., New York, NY (US)

(72) Inventors: Noam Solomon, New York, NY (US); Luis Voloch, New York, NY (US)

(73) Assignee: Immunai Inc., New York, NY (US)

( * ) Notice: Subject to any disclaimer, the term of this patent is extended or adjusted under 35 U.S.C. 154(b) by 0 days.

(21) Appl. No.: 16/998,711

(22) Filed: Aug. 20, 2020

(65) Prior Publication Data

US 2021/0057107 A1 Feb. 25, 2021

Related U.S. Application Data

(60) Provisional application No. 62/889,499, filed on Aug. 20, 2019.

(51) Int. Cl.

| | |
|---|---|
| G16H 50/50 | (2018.01) |
| G16H 10/40 | (2018.01) |
| G16H 10/60 | (2018.01) |
| G16H 50/70 | (2018.01) |
| G16H 50/20 | (2018.01) |
| G16B 5/10 | (2019.01) |
| G16B 50/00 | (2019.01) |
| G06N 3/04 | (2006.01) |
| G06N 3/08 | (2006.01) |

(52) U.S. Cl.
CPC ........... *G16H 50/50* (2018.01); *G06N 3/0445* (2013.01); *G06N 3/08* (2013.01); *G16B 5/10* (2019.02); *G16B 50/00* (2019.02); *G16H 10/40* (2018.01); *G16H 10/60* (2018.01); *G16H 50/20* (2018.01); *G16H 50/70* (2018.01)

(58) Field of Classification Search
None
See application file for complete search history.

(56) References Cited

U.S. PATENT DOCUMENTS

| | | |
|---|---|---|
| 9,940,434 B2 | 4/2018 | Kingsmore et al. |
| 2018/0233230 A1 | 8/2018 | Rubenstein et al. |
| 2019/0019085 A1 | 1/2019 | Glode et al. |
| 2019/0129819 A1 | 5/2019 | Guo et al. |
| 2020/0185063 A1 | 6/2020 | Narain et al. |

FOREIGN PATENT DOCUMENTS

WO 2020037244 A1 2/2020

OTHER PUBLICATIONS

Browning, et al., "A One-Penny Imputed Genome from Next-Generation Reference Panels", 2018 American Society of Human Genetics; The American Journal of Human Genetics 103, 338-348, Sep. 6, 2018. https://www.cell.com/ajhg/fulltext/S0002-9297(18)30242-8.

Howie, et al., "Genotype Imputation with Thousands of Genomes"; G3: Genes, Genomes, Genetics Nov. 1, 2011, vol. 1 No. 6: 457-470. https://doi.org/10.1534/g3.111.001198.

Jerez, et al., "Missing data imputation using statistical and machine learning methods in a real breast cancer problem"; Artificial Intelligence in Medicine, vol. 50, Issue 2, 2010: pp. 105-115. https://doi.org/10.1016/j.artmed.2010.05.002.

Li, et al., Genotype Imputation; Annu Rev Genomics Hum Genet. 2009 ; 10: 387-406 https://dx.doi.org/10.1146%2Fannurev.genom.9.081307.164242.

International Search Report and Written Opinion (PCT/ISA/220, PCT/ISA/210, & PCT/ISA/237) issued in PCT Application No. PCT/US2020/047148 dated Nov. 16, 2020 (14 pages).

Panjwani et al., "Improving imputation in disease-relevant regions: lessons from cystic fibrosis", NPJ Genomic Medicine, Mar. 20, 2018, pp. 1-5, vol. 3, No. 1, XP55747003, five pages.

Dorani et al., "Ensemble learning for detecting gene-gene interactions in colorectal cancer", PeerJ, Oct. 29, 2018, pp. 1-26, vol. 6, XP55746832, 26 pages.

Luengo et al., "Missing data imputation for fuzzy rule-based classification systems", Soft Computing, Oct. 14, 2011, Springer-Verlag (20 pages).

De Souto et al., "Impact of missing data imputation methods on gene expression clustering and classification", BMC Bioinformatics, Feb. 26, 2015, vol. 16, No. 64, (9 pages).

Schwender, "Statistical Analysis of Genotype and Gene Expression Data", Feb. 22, 2007 (208 pages).

Makinde, "Gene expression data classification: Some distance-based methods", Kuwait Journal of Science, Sep. 2019, pp. 31-39, vol. 46, No. 3 (10 pages).

Davoodi et al., "Mortality prediction in intensive care units (ICUs) using a deep rule-based fuzzy classifier", Journal ol Biomedical Informatics, 2018, pp. 48-59, vol. 79, Elsevier (12 pages).

Wang et al., "Identification of Differentially Expressed Genes between Original Breast Cancer and Xenograft Using Machine Learning Algorithms", genes, Mar. 12, 2018 (15 pages).

Singh et al., "DeepChrome: deep-learning for predicting gene expression from histone modifications", Bioinformatics, 2016, pp. 639-648, vol. 32, Issue 17 (10 pages).

*Primary Examiner* — G Steven Vanni
(74) *Attorney, Agent, or Firm* — Nixon & Vanderhye P.C.

(57) ABSTRACT

Methods, systems, and software provide machine learning and artificial intelligence including deep neural networks that enable the creation and operation of unique, AI-driven genomic test results augmentation through variable genetic imputation.

25 Claims, 6 Drawing Sheets

(Data Flow)

SYSTEM FOR PREDICTING TREATMENT OUTCOMES BASED UPON GENETIC IMPUTATION

1 CROSS REFERENCE TO RELATED U.S. PATENT APPLICATIONS

The present application claims priority to provisional U.S. Patent Application Ser. No. 62/889,499 filed Aug. 20, 2019, which is incorporated herein by reference in its entirety and for all purposes.

2 COPYRIGHT NOTICE

A portion of the disclosure of this patent document may contain material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice shall apply to this document: Copyright © 2019-2020, Panacea AI Corporation.

3 FIELD AND BACKGROUND OF THE TECHNOLOGY

3.1 Field of the Technology

The exemplary, illustrative, technology herein relates to systems, software, and methods for treatment options for patients with diseases with genetic markers based upon techniques for completing low-expressed genetic sequences by imputation of missing and low-expressed genetic information. The technology has use in the fields of computing, medical diagnostic tools, and the practice of medicine.

The use of artificial intelligence (AI) and deep neural networks (DNN) is transforming many fields including diagnostic and therapeutic medicine; however, while linear or simple predictive models based upon mined medical records have become prevalent, their accuracy is generally low due to the lack of detailed information available about the patient's specific disease condition and lack of ways to catch certain predictive patterns due to low input data quality.

Existing electronic health record ("EHR") mining companies extract medical records from EHR data provide structured medical information (diagnosis (DX), prescription/treatment (RX), and outcomes), but do not associate this information with known genetic sequences associated with a patient's current conditions and do not correlate clinical outcomes with the patient's collected genetic information. For example, the EHR data is often incomplete and does not contain sufficiently complete disease-associated genomic data extracted from one or more test result included in the EHR to enable existing predictive systems to accurately make predictions, contributing to the poor outcomes from these existing systems. Examples of disease-associated genomic data include tumor genomic data, or for broader assays, patient genomic data associated with a disease state.

Existing genetic-sequencing companies provide sequencing services (e.g. DNA, RNA), and provide queriable databases of known tumor types and their genetic sequences. However, these databases do not support predictive matching nor definitive matching on incomplete genomic data, nor do they provide recommended treatment (RX) and predicted outcome data.

In addition, these existing companies use common genomic sequencing techniques that frequently do not sequence enough of the available genomic information to enable a complete and accurate diagnosis and recommendation of the most effective therapy as the genomic information comprises one or more partially (either incomplete or low expression rate) expressed portions, or the available genetic sequence information does not permit identification of the most effective therapy. In some cases, the information needed to make an accurate determination has not been identified, in others the testing results are incomplete, or the sequencing technology has sensitivity limitations resulting in results using these test results that suggest several possible treatments and outcomes without differentiation as to which course of treatment may produce a better outcome for a particular patient. The ability to narrow the list of potential treatments and outcomes to the selected effective therapy (or therapies) is needed to prevent ineffective trials in the treatment regime; these trials increase costs and may decrease the survivability of the patients. Furthermore, the results of analysis of the medical records and treatment outcomes provides for earlier identification of potential success and failure of a current treatment regime.

For example, as a result of these limitations in the current technologies, currently only about 30%-40% of patients treated with a specific immunotherapy see a partial or complete response to the treatment, which increases treatment timelines, allows disease progression, resulting in increased health care costs and exposes patients to unnecessary treatments and side effects, and reduces their overall quality of life Similar limitations are present for many disease diagnosis/treatment pairs.

What is needed is a system that improves the accuracy with which a physician can select an immunotherapy treatment for a specific patient, in which the selected treatment is more likely than not to be effective, and according to which the patient outcomes can be monitored to quickly determine if the treatment is having a beneficial effect on disease progression or if an alternative treatment might be indicated instead.

4 SUMMARY OF THE EMBODIMENTS

The technology herein addresses the deficiencies and issues reviewed above by providing methods, systems, and software that enable the creation and operation of unique, AI-driven genetic test results augmentation via novel imputation techniques and provides an increased accuracy of prediction of patient treatment outcomes.

An embodiment of a system for variably imputing genetic information into a collected genetic data set may comprise storage access circuitry structured to read an input genetic data set comprising genetic expression data including genetic test results, and to read at least one imputation data set from a database, the imputation data set comprising one or more imputation technique definitions for variably imputing genetic data; and an imputation engine coupled to a storage access circuitry, the imputation engine applying the one or more imputation technique definitions from the at least one imputation data set to a collected genetic data set to variably impute genetic data and create an resulting genetic data set, wherein the storage access circuitry is further configured to output the resulting genetic dataset.

The imputation engine may select one or more imputation technique definitions from one or more trained models stored in the database and/or an imputation technique based in part upon at least one of a collected diagnosis, a collected treatment, a collected patient demographic, and/or a collected genetic datum that is part of a collected genetic data set.

The imputation engine may be further structured to provide an imputation technique by a using a selected trained model that produces changes in the collected genetic data set to produce a changed genetic data set.

At least one imputation data set may be registered based at least in part upon a collected diagnosis, collected treatment, collected patient demographic, and/or a collected genetic datum present in the collected genetic data set. The at least one imputation data set may comprise one or more imputation rules.

The resulting genetic dataset may comprise one or more of the input genetic data set(s), and a specified alteration to the input genetic data set the imputation engine makes in response to execution of the one or more imputation rules and/or the input genetic data set and added genetic expression data and/or the input genetic data set and at least one changed expression level of genetic expression data and/or the input genetic data set with at least one removed genetic expression datum.

The one or more imputation rules may comprise an expression that is evaluated to determine if a genetic imputation action specified by the one or more imputation rules is to be performed.

The imputation engine may be configured to evaluate the expression by an imputation rule execution function to determine a Boolean inclusion decision for an imputation rule. The Boolean inclusion decision may result in an imputation action specified in an imputation rule being executed by the imputation engine if the expression is determined to be true.

An embodiment of a method and/or computer readable media for variably imputing genetic information into a collected genetic data set may comprise reading an input genetic data set comprising genetic expression data including genetic test results, reading at least one imputation definition from a database, the imputation definition comprising one or more imputation technique definitions for variably imputing genetic data, applying the one or more imputation definition(s) to a collected genetic data set to variably impute genetic data, and outputting the variably imputed genetic data.

The method and/or computer readable media may include selecting the one or more imputation definitions from one or more trained models stored in the database and/or selecting an imputation definition based in part upon a collected diagnosis and/or a collected genetic datum in the collected genetic data set and/or executing a selected imputation definition by executing a trained model that produces changes in the collected genetic data set to produce a changed genetic data set and/or selecting the at least one imputation data set based at least in part upon a collected diagnosis and/or collected genetic data present in the collected genetic data set.

The at least one imputation data set may comprise one or more imputation rules.

The outputted genetic data may comprise at least one of the input genetic data set and at least one specified alteration to the input genetic data set in response to the execution of an imputation rule and/or the input genetic data set and added genetic expression data and/or the input genetic data set and at least one changed expression level of genetic expression data and/or the input genetic data set with at least one removed genetic expression datum.

The one or more imputation rules may comprise an expression that is evaluated to determine if a genetic imputation action specified by the one or more imputation rules is to be performed.

The method and/or computer readable media may further comprise evaluating the expression by an imputation rule execution function to determine a Boolean inclusion decision for the imputation rule. The Boolean inclusion decision may result in the imputation action specified in the imputation rule being executed if the expression evaluates as true.

An embodiment of a method and/or computer readable media of predicting a disease outcome may comprise selecting, from a database of genetic markers, a set of genetic markers corresponding to a disease or immune state; collecting a set of genetic marker values by parsing a patient electronic health record (EHR); generating one or more imputed genetic marker values by applying one or more pre-determined rules to one or more of the collected genetic marker values; generating a set of genome-specific trained model predicted outcomes by: for each collected genetic marker value: selecting, from a set of genome-specific trained models, at least one genome-specific trained model corresponding to the collected genetic marker value; using each of the selected the genome-specific trained model(s) to generate a genome-specific trained model predicted outcome, thereby generating a set of genome-specific trained model predicted outcomes; and using a second trained model to generate an overall outcome prediction using model inputs that comprise the set of genome-specific trained model predicted outcomes.

An embodiment of a method and/or computer readable media of recommending a treatment or diagnostic test may comprise selecting, from a database of genetic markers, a set of genetic markers corresponding to a disease or immune state; collecting a set of genetic marker values by parsing a patient electronic health record (EHR); generating one or more imputed genetic marker values associated with one or more of the collected genetic marker values; generating a set of genome-specific trained model predicted outcomes by: for each collected genetic marker value: selecting, from a set of genome-specific trained models, at least one genome-specific trained model corresponding to the collected genetic marker value; executing each of the selected the genome-specific trained model(s) to generate a genome-specific trained model predicted outcome, thereby generating a set of genome-specific trained model predicted outcomes; executing a second trained model to identify one or more genome-specific trained model predicted disease states and/or outcomes, and recommending one or more identified treatments and/or diagnostic tests on the basis of the one or more predicted disease states and/or outcomes.

The method and/or computer readable media may further include prescribing the recommended one or more identified treatments and/or diagnostic tests.

The recommending may include identifying one or more diagnostic tests and/or treatments for a predicted disease state.

The method and/or computer readable media may further include using a selected trained model to identify genetic imputations.

The method and/or computer readable media may further include selecting one or more rules, and evaluating an expression associated with each rule to identify genetic imputations to be performed.

An embodiment of a predictor system for predicting a disease outcome may comprise at least one processor configured to perform operations comprising: selecting, from a database of genetic markers, a set of genetic markers corresponding to a disease or immune state; collecting a set of genetic marker values by parsing a patient electronic health record (EHR); generating one or more imputed genetic marker values by applying one or more pre-determined rules to one or more of the collected genetic marker values; generating a set of genome-specific trained model predicted outcomes by: for each collected genetic marker value: selecting, from a set of genome-specific trained models, at least one genome-specific trained model corresponding to the collected genetic marker value; using machine learning based on each of the selected the genome-specific trained model(s) to generate a genome-specific trained model predicted outcome, thereby generating a set of genome-specific trained model predicted outcomes; and using a second trained model to generate an overall outcome prediction using model inputs that comprise the set of genome-specific trained model predicted outcomes.

An embodiment of a recommender system for recommending a treatment or diagnostic test may comprise at least one processor configured to perform: selecting, from a database of genetic markers, a set of genetic markers corresponding to a disease or immune state; collecting a set of genetic marker values by parsing a patient electronic health record (EHR); generating one or more imputed genetic marker values associated with one or more of the collected genetic marker values; generating a set of genome-specific trained model predicted outcomes by: for each collected genetic marker value: selecting, from a set of genome-specific trained models, at least one genome-specific trained model corresponding to the collected genetic marker value; executing each of the selected the genome-specific trained model(s) to generate a genome-specific trained model predicted outcome, thereby generating a set of genome-specific trained model predicted outcomes; executing a second trained model to identify genome-specific trained model predicted disease state and/or outcomes; and recommending one or more of the identified treatments and/or tests on the basis of the predicted disease state and/or outcomes.

An output device may output a prescription for the recommended one or more identified treatments and/or tests.

The at least one processor may be further configured to identify one or more tests and/or treatments for a predicted disease state.

Machine learning hardware may use a selected trained model to identify genetic imputations.

The at least one processor may be further configured for selecting one or more rules, and evaluating an expression associated with each rule to identify genetic imputations.

An embodiment of a method and/or computer readable media for improving the performance of a disease outcome prediction machine by generating input features for the disease outcome prediction machine comprising observed and imputed values of genetic markers may comprise selecting, from a database of genetic profiles, a genetic profile comprising one or more genetic marker values, each corresponding to a particular disease or condition; mining a patient electronic health record (EHR) for observed genetic marker values that comprise the selected genetic markers; and if one or more values of genetic markers that comprise the selected genomic profile require modification from value of genetic markers in the observed genetic markers, performing targeted imputation to produce imputed genetic marker values; or if one of more values of genetic markers that comprise the selected genetic profile are missing from both the observed genetic marker values and the imputed genetic marker values, generating one or more recommendations for deeper or targeted sequencing to create additional observed genetic marker values.

An embodiment of a disease outcome prediction machine for generating input features comprising observed and imputed values of genetic markers may comprise: a selector circuit that selects, from a database of genetic profiles, a genetic profile comprising genetic marker values each corresponding to a particular disease or condition, a data mining circuit that mines a patient electronic health record (EHR) for observed genetic marker values that comprise the genetic markers, and at least one processor configured to: (a) perform targeted imputation to produce imputed genetic marker values if one or more values of genetic markers that comprise the genomic profile are missing from the observed genetic markers, and (b) generate one or more recommendations for deeper or targeted sequencing to generate additional observed genetic marker values if one of more values of genetic markers that comprise the genetic profile are missing from both the observed genetic marker values and the imputed genetic marker values.

An embodiment of a system for processing patient data to create imputation trained models may comprise a patient data collection engine configured to read and parse at least one electronic health record (EHR) dataset stored in a database comprising data from electronic health records (EHRs), the patient data collection engine comprising a patient EHR mining engine configured to: receive, from the database of EHRs dataset, a plurality of patient EHRs datasets, receive from a database of genetic markers, a set of genetic markers associated with at least one of the data elements in the received datasets; and mine the plurality of patient EHRs datasets for observed genetic marker values comprising observed genetic marker values, where the patient data collection engine is configured to interface with a hardware genetic material processor comprising a machine learning-based autoencoder configure to produce at least one trained model configured and trained to produce imputed genetic marker values based on observed genetic marker values, wherein each of the imputed genetic marker values corresponds to a received genetic marker.

The autoencoder may comprise a neural network selected from the group consisting of auto-encoder, recurrent neural network, and convolutional neural network. The auto-encoder may be configured to create one or more rule-based encodings of the trained model.

The system may further comprise a database of methods for generating genetic data, and a low abundance method recommendation engine configured to recommend one or more methods for generating genetic data when genetic markers are missing from both observed and imputed genetic markers.

An embodiment of a method and/or computer readable media for processing patient data to create imputation trained models may comprise providing a database of genetic markers for imputation, providing a database of patient electronic health records (EHRs) datasets operating a patient EHR mining engine to receive, from the database of patient EHRs datasets, a plurality of patient EHRs datasets, receive from the database of genetic markers, a set of genetic markers associated with a genetic marker in the patient EHR dataset(s); and mine the plurality of patient EHRs datasets for observed genetic marker values comprising observed genetic marker values associated with the received genetic marker information, using a machine learning-based deep neural network to produce at least one trained model configured and trained to produce imputed genetic marker values based on observed genetic marker values wherein each of the imputed genetic marker values corresponds to a observed genetic marker, and writing the at least one trained model to a data storage.

The neural network may be selected from the group consisting of an auto-encoder, a recurrent neural network, and a convolutional neural network. The method and/or computer readable media may further include operating the auto-encoder to create one or more rule-based encodings of the trained model. The method and/or computer readable media may further comprise providing a database of methods for generating genetic data, and using a low abundance method recommendation engine to recommend one or more methods for generating additional genetic data when low abundance or missing genetic markers are identified both the observed and imputed genetic markers.

An embodiment of a system for imputing genetic marker values may comprise a patient electronic health record (EHR) mining engine configured to: receive, from the database of EHRs datasets, a patient EHR, comprising genetic marker data created using one or more particular assay arrays; and mine the patient EHR dataset for observed genetic marker values; a long short-term memory (LSTM) autoencoder comprising: at least one inner layer comprising a first set of weighted coefficients selected based on a set of genetic markers that are not included in the one or more particular assay arrays, a second set of weighted coefficients selected based on polygenic risk scores associated with auto-immune pre-distribution, a third set of weighted coefficients selected based on polygenic risk scores associated with cancer pre-distribution, and a fourth set of weighted coefficients selected based on genetic markers selected from a database of genetic markers and statistics; wherein the LSTM autoencoder is configured to produce imputed values of genetic markers based on at least one observed genetic marker values.

The system may comprise writing the imputed values as a rule to a database.

The LSTM autoencoder may further comprise an input layer comprising genetic markers identified by the particular assay arrays; and an output layer that provides genetic marker values that include imputed values of at least one genetic markers.

The set of genetic markers that are not included in the one or more particular assay arrays may comprise a set of human leukocyte antigen (HLA) single nucleotide polymorphisms (SNPs); and the output layer provides the complete genome of the set of HLA-A and HLA-B genes and/or the output layer may provide a complete genome.

The LSTM autoencoder may be trained with data selected from: genetic markers identified by one or more particular assay arrays; genetic markers that are not included in the one or more particular assay arrays; polygenic risk scores associated with at least one of auto-immune and cancer pre-distribution; and genetic markers selected from a database of genetic markers and statistics.

The LSTM autoencoder may be trained with data selected from genetic markers identified by one or more particular assay arrays and/or data selected from genetic markers that are not included in the one or more particular assay arrays and/or data selected from polygenic risk scores associated with at least one of auto-immune and cancer pre-distribution and/or data selected from genetic markers selected from a database of genetic markers and statistics.

An embodiment of a method and/or computer readable media for imputing genetic marker values may comprise receiving, from the database of electronic health records (EHRs), a patient EHR dataset comprising genetic marker data created using one or more particular assay arrays; mining the patient EHR dataset for observed genetic marker values; and operating a long short-term memory (LSTM) autoencoder comprising at least one inner layer comprising a first set of weighted coefficients selected based on a set of genetic markers that are not included in the one or more particular assay arrays, a second set of weighted coefficients selected based on polygenic risk scores associated with auto-immune pre-distribution, a third set of weighted coefficients selected based on polygenic risk scores associated with cancer pre-distribution, and a fourth set of weighted coefficients selected based on genetic markers selected from a database of genetic markers and statistics; wherein the LSTM autoencoder produces imputed values of genetic markers based on the observed genetic marker values.

The method and/or computer readable media may include writing the imputed values as a rule to a database.

The set of genetic markers that are not included in the one or more particular assay arrays may comprise a set of human leukocyte antigen (HLA) single nucleotide polymorphisms (SNPs); and the output layer provides the complete genome of the set of HLA-A and HLA-B genes.

The set of genetic markers that are not included in the one or more particular assay arrays may comprise a set of human leukocyte antigen (HLA) single nucleotide polymorphisms (SNPs); and the output layer provides a complete genome.

The method and/or computer readable media may further comprise training the LSTM autoencoder with data selected from: genetic markers identified by one or more particular assay arrays; genetic markers that are not included in the one or more particular assay arrays; polygenic risk scores associated with at least one of auto-immune and cancer pre-distribution; and genetic markers selected from a database of genetic markers and statistics.

The method and/or computer readable media may further comprise training the LSTM autoencoder with data selected from genetic markers identified by one or more particular assay arrays.

The method and/or computer readable media may further include training the LSTM autoencoder with data selected from genetic markers that are not included in the one or more particular assay arrays and/or data selected from polygenic risk scores associated with at least one of auto-immune and cancer pre-distribution and/or data selected from genetic markers determined from a database of genetic markers and statistics.

An embodiment of a method and/or computer readable media for generating imputation trained models may comprising collecting a set of collected genetic marker values from a training database, imputing missing or low expressed genetic marker values, creating processed collected data, and creating a trained model from the processed collected data.

Creating the one or more imputation trained models may include training a LSTM autoencoder with a training dataset comprising: genetic markers identified by one or more particular assay arrays; genetic markers that are not included in the one or more particular assay arrays; polygenic risk scores associated with at least one of auto-immune and cancer pre-distribution; and genetic markers selected from a database of genetic markers and statistics.

The trained LSTM auto encoder may comprises an input layer comprising SNPs identified by particular assay arrays, an inner layer comprising selected weights (loss functions) comprising a set of SNPs (e.g. HLA SNPs) that are not part of the selected assay arrays, and weights associated with each SNP; an inner layer comprising selected weights (loss functions) comprising selected weights (loss functions) comprising Parameters from Polygenic risk scores associated with auto-immune diseases; an inner layer comprising selected weights (loss functions) comprising parameters from Polygenic risk scores associated with cancer predisposition; an inner layer comprising selected weights (loss functions) comprising parameters identified in the literature (e.g. Stanford GWAS, literature searches); and an output layer that provides the complete genome of HLA-A and HLA-B genes.

Training the one or more imputation trained models may include generating, with the trained LSTM autoencoder, one or more entries in an imputation possibilities database where each entry includes a rule for generating at least one imputed genetic marker value(s) based on at least one observed genetic marker value; and training a trained expert rules module to produces an imputed genetic marker value using a rule and at least one observed genetic marker value.

An embodiment of a system for generating imputation trained models may comprise at least one processor configured to collect a set of collected genetic marker values from a training database, at least one neural network configured to impute missing or low expressed genetic marker values, creating processed collected data, and a machine learning device configured to create a trained model from the processed collected data.

The machine learning device may include a LSTM autoencoder with a training dataset comprising: genetic markers identified by one or more particular assay arrays; genetic markers that are not included in the one or more particular assay arrays; polygenic risk scores associated with at least one of auto-immune and cancer pre-distribution; and genetic markers selected from a database of genetic markers and statistics.

The trained LSTM auto encoder may comprise an input layer comprising SNPs identified by particular assay arrays, an inner layer comprising selected weights (loss functions) comprising a set of SNPs (e.g. HLA SNPs) that are not part of the selected assay arrays, and weights associated with each SNP; an inner layer comprising selected weights (loss functions) comprising selected weights (loss functions) comprising Parameters from Polygenic risk scores associated with at least one auto-immune disease; an inner layer comprising selected weights (loss functions) comprising parameters from Polygenic risk scores associated with cancer pre-disposition; an inner layer comprising selected weights (loss functions) comprising parameters identified in the literature (e.g. Stanford GWAS, literature searches); and an output layer that provides the complete genome of HLA-A and HLA-B genes.

The machine learning device may include a trained LSTM autoencoder configured to generate one or more entries in an imputation possibilities database where each entry includes a rule for generating at least one imputed genetic marker value(s) based on at least one observed genetic marker value; and a trained expert rules module trained to produce an imputed genetic marker value using a rule and at least one observed genetic marker value.

An embodiment of a system for imputing genetic marker values may comprise a database of rules for generating imputed genetic marker values and imputed strength of the genetic marker values based on information that includes values of observed genetic marker values; and a rules engine for selecting one or more rules from the database of rules and for using the selected one or more rules to produce imputed genetic marker values.

An embodiment of a system for improving the performance of a disease outcome prediction machine by generating input features for the disease outcome prediction machine comprising observed and imputed values of genetic markers may comprise a storage access circuit configured to select, from a database of genetic profiles, a genetic profile comprising genetic marker values corresponding to a particular disease or condition, a patent database access processor configured to mine a patient electronic health record (EHR) dataset(s) for observed genetic marker values that comprise the selected genetic markers, and an imputation engine coupled to the patient database access processor and the storage access circuit, the imputation engine being configured to perform operations comprising if one or more values of genetic markers that comprise the selected genomic profile are missing from the observed genetic markers, performing targeted imputation to produce imputed genetic marker values, and if one of more values of genetic markers that comprise the selected genetic profile are missing from both the observed genetic marker values and the imputed genetic marker values, generating one or more recommendations for deeper or targeted sequencing to produce additional observed genetic marker values.

An embodiment of a method and/or computer readable media for imputing genetic marker values may comprise collecting a set of collected genetic marker values, generating a set of missing genetic markers that includes selected genetic markers that are not included in a set of collected genetic marker values, including selecting the genetic marker values from a database of genetic markers associated with a disease state; and imputing at least one genetic marker value for one or more of the genetic markers in the set of missing genetic markers.

Collecting genetic marker values may include parsing a patient electronic health record (EHR) dataset to select a set of collected genetic marker values and/or reading genetic information from a genomic testing device.

Imputing a genetic marker value may include selecting from among a set of imputation trained models, a particular imputation trained model that has been trained to impute only the selected set of genetic markers; and executing the particular imputation trained model to produce at least one imputed genetic marker value.

Imputing a genetic marker value may include selecting, from an imputation possibilities database, one or more imputation rules wherein each imputation rule corresponds to one or more collected genetic markers and to one or more genetic markers; executing, with a trained imputation model, the one or more imputation rules to produce one or more imputed genetic marker values.

Executing the one or more imputation rules may include generating an imputed strength of expression associated with one or more imputed genetic marker values.

An embodiment of a method and/or computer readable media of generating imputed genetic markers for inclusion in a processed collected dataset corresponding to a disease or immune state, may comprise creating one or more imputation trained models to produce imputed values for one or more genetic markers wherein the one or more genetic markers consist of genetic markers that are associated with a specific disease or immune state; collecting observed disease/immune state genetic markers from a collected dataset; imputing genetic markers related to the disease/immune state and the collected data, and including the produced imputed data into a processed collected dataset.

The imputing may further comprise selecting one or more imputation trained models for use, and executing one or more of the imputation trained models to produce imputed genetic marker values corresponding to missing genetic markers in the observed genetic markers and/or identifying a database of imputation rules associated with the identified disease/immune state, selecting one or more imputation rules to evaluation on the basis of the identified disease/immune state, and evaluating the selected rules, and if a rule evaluation evaluates as TRUE, implement the rule action to effect the imputation.

An embodiment of a system for imputing genetic marker values may comprise at least one processor configured to collect a set of collected genetic marker values, the processor further configured to produce a set of missing genetic markers that includes selected genetic markers that are not included in a set of collected genetic marker values, and to select the genetic marker values from a database of genetic markers associated with a disease state; and an imputation engine configured to impute at least one genetic marker value for one or more of the genetic markers in the set of missing genetic markers.

The processor may be configured to parse a patient electronic health record (EHR) dataset to select a set of collected genetic marker values and/or to read genetic information from a genomic testing device.

The imputation engine may comprise a selecting circuit configured to select from among a set of imputation trained models, a particular imputation model that has been trained to impute only the selected set of genetic markers; and an execution circuit that executes the particular imputation model to produce the imputed genetic marker value and/or an imputation possibilities database that provides one or more imputation rules wherein each imputation rule corresponds to one or more collected genetic markers and to one or more imputable genetic markers; and a trained imputation model that executes the one or more imputation rules to produce one or more imputed genetic marker values.

The trained imputation model produces an imputed strength of expression associated with one or more imputed genetic marker values.

An embodiment of a system of generating imputed genetic markers for inclusion in a processed collected dataset corresponding to a disease or immune state, may comprise one or more imputation trained models configured to produce imputed values for one or more genetic markers wherein the one or more genetic markers consist of genetic markers that are associated with the disease or immune state; a collected dataset providing collected observed disease/immune state specific genetic markers; an imputation engine that imputes genetic markers related to the disease/immune state and the collected data; and an output device that includes the produced imputed data into a processed collected dataset.

The imputation engine may further comprise a selector that selecting one or more imputation trained models for use, and an execution core that executes one or more of the imputation trained model(s) to produce one or more imputed genetic marker values corresponding to any genetic markers missing from the observed genetic markers.

The imputation engine may comprise a database of imputation rules associated with genetic markers of an identified disease/immune state, a selector that selects one or more imputation rules to evaluation on the basis of the identified disease/immune state, and a processor that evaluates the selected rules, and if a rule evaluation evaluates as TRUE, implements the rule action to effect the imputation.

The above techniques may be used individually or in combination. For example, techniques and structures of an embodiment of a system or method and/or computer readable media for variably imputing genetic information into a collected genetic data set may be used with techniques and structures of an embodiment of a method and/or computer readable media of predicting a disease outcome and/or techniques and structures of an embodiment of a method and/or computer readable media of recommending a treatment or diagnostic test and/or techniques and structures of an embodiment of a predictor system for predicting a disease outcome and/or n embodiment of a recommender system for recommending a treatment or diagnostic test and/or techniques and structures of an embodiment of a method and/or computer readable media for improving the performance of a disease outcome prediction machine by generating input features for the disease outcome prediction machine and/or a disease outcome prediction machine for generating input features comprising observed and imputed values of genetic markers and/or techniques and structures of an embodiment of a system or method and/or computer readable media for processing patient data to create imputation trained models and/or techniques and structures of an embodiment of a system or method and/or computer readable media for imputing genetic marker values and/or techniques and structures of an embodiment of a system or method and/or computer readable media for generating imputation trained models and/or techniques and structures of an embodiment of a system for generating imputation trained models and/or techniques and structures of an embodiment of a system or method and/or computer readable media for imputing genetic marker values and/or techniques and structures of an embodiment of a system for improving the performance of a disease outcome prediction machine by generating input features for the disease outcome prediction machine comprising observed and imputed values of genetic markers and/or techniques and structures of an embodiment of a method and/or computer readable media of generating imputed genetic markers for inclusion in a processed collected dataset corresponding to a disease or immune state and/or techniques and structures of an embodiment of a system of generating imputed genetic markers for inclusion in a processed collected dataset corresponding to a disease or immune state.

These and other aspects and advantages will become apparent when the Description below is read in conjunction with the accompanying Drawings.

5 BRIEF DESCRIPTION OF THE DRAWINGS

The features of the present technology will best be understood from a detailed description of the technology and example embodiments thereof selected for the purposes of illustration and shown in the accompanying drawings.

6 DESCRIPTION OF SOME EMBODIMENTS OF THE TECHNOLOGY

6.1 High Level Overview

Figure 1:
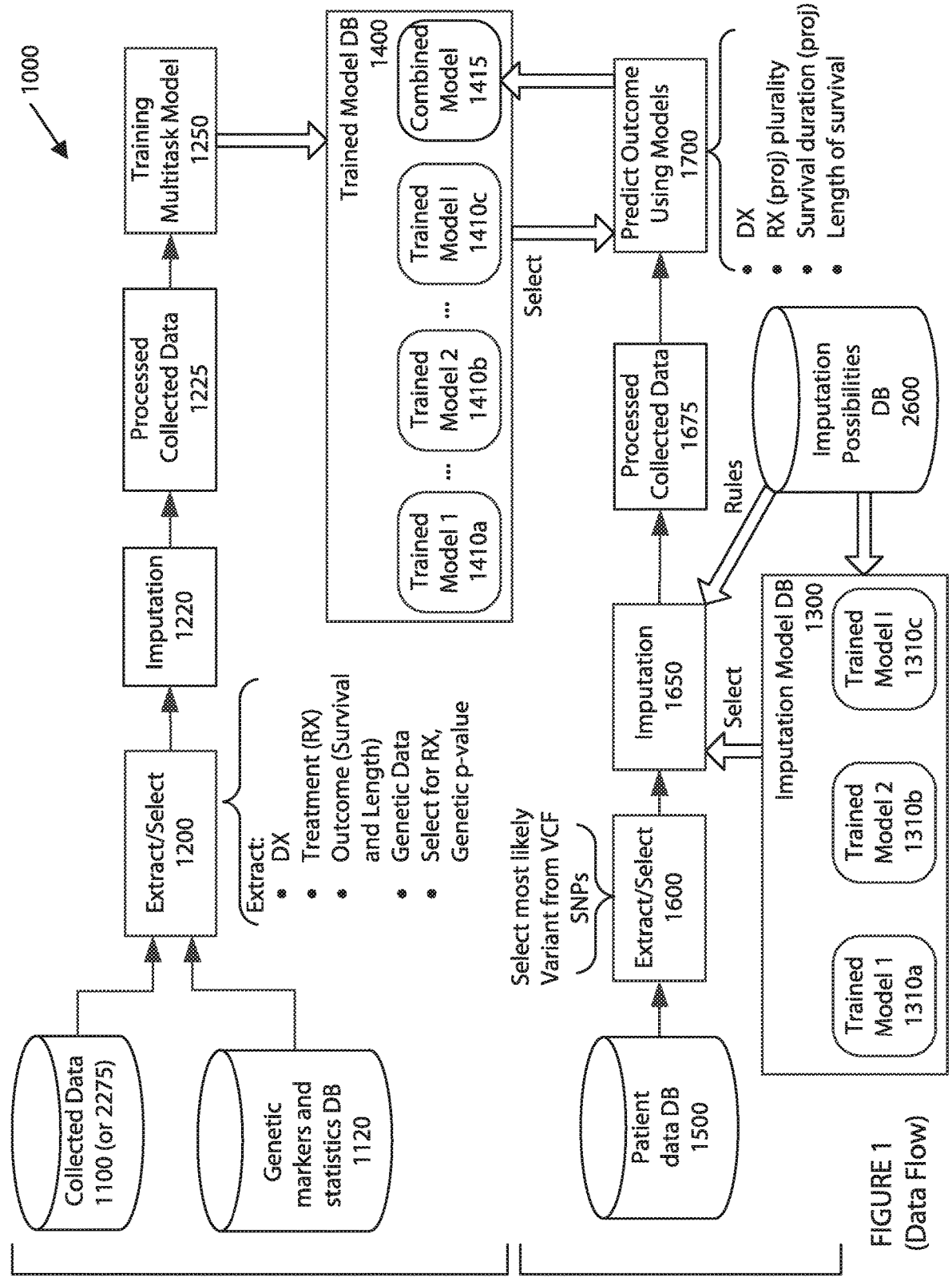
FIG. 1 illustrates an exemplary system architecture/data flow for training and diagnostic use of the system as implemented by the current technology.

The technologies support accurate recommendation of specific therapies, and the prediction of therapy patient health outcomes in spite of the wide variation in patient immune system responses and known immunotherapy outcomes by using a collection of machine learning techniques for diagnosis (DX)/treatment (RX) and outcome prediction, utilizing a combination of selected genetic imputation and trained expert systems, and ongoing monitoring of patient progress to determine the correlation between predicted and actual patient outcomes.

The exemplary technologies presented herein use artificial intelligence (AI) and deep neural network (DNN)-based techniques as applied to complex datasets comprising the combination of medical data obtained from EHR mining, collection of detailed genetic data further comprising one or more of DNA tumor sequences, a subset of the circulating free DNA (cfDNA) obtained from blood and/or plasma samples comprising DNA shed from tumor cells, tumor imaging, immune system genomic data, genetic sequencing of microbiome, and other similar immunological assays, the set of which is enhanced using a novel genetic (e.g. genome and microbiome) imputation methodology that increases the robustness of the input data set for a particular patient using imputation strategies and methods that are less resource intensive than existing methods. The exemplary technologies presented herein improve the results obtained using a trained deep neural network for predicting disease progression and outcomes many fold without incurring the increased computing resource costs required by existing imputation methods.

The ongoing monitoring techniques permit the system to determine how an individual is responding to a specific therapy and refine the prediction on the basis of observed response and any additional test results that become available.

The exemplary technologies described herein extend EHR mining results to include complete outcome information for historic cases (length of survival, disease progression timelines), as well as enabling the ongoing collection and inclusion of genetic data that may not have been available in early stages of treatment. The EHR mining component further supports the inclusion of patient-specific markers (e.g., genetic markers, immune-specific markers, microbiome markers), which are used by the current technology as part of its data completion (e.g. imputation), predictive, and recommender features. When the system determines that conditions exist where insufficient information is provided in the mined EHR dataset that cannot be resolved by the imputing features of the methods described herein, the system recommends further activities (e.g. tests, procedures) capable of generating additional information in order to improve the predictive and/or recommendation outcomes of the system (e.g. additional or deeper sequencing), These recommended tests and procedures are identified in a database (e.g. recommended tests database, FIG. 4, 3775). Insufficient information includes conditions that produce imputation, predictive, or recommendations with low confidence, or confidence below a defined threshold stored in a system configuration. The identified tests may be used to perform additional testing on previously collected and retained biological samples or may include collecting new samples from a patient. For example, the system may determine that it is unable to produce a recommended therapy with a confidence above a preset threshold of 75%, and thus generates a recommendation for additional sequencing tests (as described below).

Because common genomic sequencing techniques often do not sequence enough of the patient's genetic information to enable identification of an effective therapy, taking into account all available information, or the testing that has been performed to date does not identify a sufficiently robust sequence or set of sequences that enable the identification of an effective therapy, the described technology uses a data completion model for genetic imputation to enhance the collected data in order to improve the technologies' predictive outcomes, which reduces the number of potential treatments considered by more completely associating the state of the collected data, the treatments performed, and known outcomes in other cases, permits the system to more accurately identify likely effective treatments and their predicted outcomes. The ability to narrow the list of potential treatments and outcomes to one or more likely effective therapies associated with specific outcomes reduces the administration of ineffective and costly immunotherapies or other treatments as part of the treatment regime.

Lastly, the described technology provides for ongoing monitoring of the patient's progress on a specific immunotherapy, which enables the treating physician to more quickly determine that a patient's tumor is not responding to that therapy, leading to earlier termination of ineffective treatment regimens and modification of the treatment plan. Existing prediction systems do not track a patient's progress over time, are not capable of providing early indications that a treatment is not working and that an alternative treatment should be considered. The training, prediction, and tracking capabilities of these types of systems may be improved to >62% accuracy by using the techniques and technologies described herein by highlighting a large fraction of patients that are at risk of non-response.

Thus, the described system facilitates improved selection of effective immunotherapy treatment options for each individual patient, in which the selected treatment is more likely to be effective, and monitors patient outcomes in order to quickly determine if the treatment is having the expected effect or if an alternative treatment would be more effective.

The accuracy of the machine learning and prediction/recommendation process steps are optionally improved by pre-processing collected data to impute missing, incomplete, and/or low expressed genetic information in the collected dataset, creating a pre-processed collected dataset. This allows the machine learning models to more accurately predict outcomes and recommend treatments by eliminating conditions in which there is insufficient distinguishing data in the patient's collected data. The imputation process imputes genetic data using one or more imputation trained models configured and selected to determine missing, incomplete, and/or low expressed genetic data. In this way, each trained model is an imputation definition for a specific condition. In some embodiments, a general imputation may be performed where all imputable genetic information is imputed by the system. In some embodiments, a specific imputation may be performed, such a specific imputation operation that imputes genetic information associated with one or more particular disease conditions. The specific imputation alternative embodiment allows the prediction model to save computing resources by not imputing genetic information that is not needed for prediction and/or recommendation activities. Limiting the process to imputing only missing genetic information associated with one or more specific diseases further increases the resolution and accuracy when imputing low abundance genetic markers that may be missing in the collected genomic data. The prediction process further imputes missing genetic data associated with one or more identified diseases, and generates a prediction value representing confidence in, or strength of, imputation, using one or more imputation possibility rules. These rules are generated during model training (using training datasets) as described below. This allows the system to use a low-resource rules-matching imputation method rather than employing a known resource-intensive imputation method when processing collected genomic data.

The described system includes the hardware and software components necessary for processing a variety of clinical data and predicting patient outcomes for immunotherapeutic treatment of disease, comprising at least one trained predictive model which in an exemplary embodiment is a comprising a deep neural network of at least 6 layers, in which the trained predictive model is trained on a combination of patient EHR data and/or directly read genetic data and predicts at least one of the following: a disease diagnosis, the effectiveness of a disease treatment, a disease outcome, a disease progression over time, or disease survival.

In more specific embodiments, the described system and methods predict outcomes of therapies on disease and/or immune states treatable with specific therapies including predicted outcomes of these specific therapies. In these more specific embodiments, the described system and methods comprise collecting incomplete patient genomic data, imputing missing genomic data with the collected genomic data to produce processed collected genomic data, and using the processed collected genomic data with the trained predictive model in order to determine one or more of a disease diagnosis, the effectiveness of a disease treatment, a disease outcome, a disease progression over time, or disease survival.

These and other aspects and advantages will become apparent when the Description below is read in conjunction with the accompanying Drawings.

6.2 Definitions

The following definitions are used throughout, unless specifically indicated otherwise:

| TERM | DEFINITION |
| --- | --- |
| Genetic data | Germline sequence data, mutation data, single cell RNA sequencing (scRNAseq), microbiome sequencing, metabolomic data, genetic and genomic test results. |
| Collected dataset | Genetic information extracted from one or more EHR record (s) and/or collected directly from sources of genetic information. |
| Produce | Create, modify, or remove a genomic value under the control of the imputation process. Producing a dataset includes creating a dataset including at least one produced genomic value. |
| EHR | Electronic Health Record Comprises medical records including diagnosis (DX) and treatment (RX) information and standard medical laboratory test results, as well as genetic and genomic test results that comprising one or more of measured patient RNA, DNA, and microbiome data. |

-continued

| TERM | DEFINITION |
| --- | --- |
| Genetic profile | A set comprising one or more genetic marker values. |
| SNP | Single Nucleotide Polymorphism occurs where there is a substitution of a single nucleotide at a specific position in the genome, and the substitution is present in 1% or more of the population. SNPs are predictors of susceptibility to some genetic-based diseases such as sickle-cell anemia and cystic fibrosis, and also predictors of how the body will respond to treatment. |
| VCF | Variant Call Format, a standardized text file format for representing SNP and other genetic information. |
| Microbiome | The combined genetic material of the microorganisms present in a particular physiological environment such as, for example, the gut or the skin. |
| Disease areas | Auto-immunity, oncology (e.g. cancers (general), breast cancer, |
| Diagnosis (DX) | The identification of a disease or illness, sometimes associated with a well-known identifier such as an ICD code. |
| Treatment (RX) | Medical care provided to a patient for an illness or injury, sometimes associated with a well-known identifier such as an ICD code. Treatments may include, for example, immunotherapy, chemotherapy, radiation, anti-inflammatory drugs. |
| Outcome | The effect of a treatment on a patient's health and/or disease course. |

6.3 Detailed Description of Exemplary Embodiments 6.3.1 Data Flow for Exemplary Training Mode Operation FIG. 1 illustrates an exemplary data flow and interaction (1000) between the training and prediction systems and provides a general example of how the system operates to produce improved results.

Machine learning techniques are typically ineffective, or at best, partially effective, in analyzing patient EHR data for determining the best outcome for patients with specific cancer types, treatments, and outcomes because the training datasets often do not have sufficient genetic information in the encoded patient EHR data to establish necessary correlation(s).correlations. Thus, the models produced by training a machine learning system on this type of data do not accurately predict treatment/outcome for a specific patient with a definitive diagnosis and supporting lab work. Improvements can be made to the data flows in the model training processes and the patient EHR processing in order to produce a system that can accurately predict the outcome of various treatment regimes.

The training process improvements include the combination of parsing EHR records to generate a training dataset storage database (2275) along with statistical significance data that indicates significance of genetic information that may be found in the parsed EHR data. Exemplary statistical significance data includes p-value summary statistics data that indicate the relevance of particular genetic markers, and/or relevance of traits associated with the genetic markers, to particular diseases or conditions. The statistical significance data are taken from a database of genetic markers and their associated statistics (e.g. database 1120). The database may be generated by extracting summary statistics, including p-values, from Genome Wide Association Studies (GWASs), both public and private, and in particular, from GWASs that are related to specific disease pathologies, such as oncology and immunology. GWAS (genome-wide association study) identifies inherited genetic variants associated with a risk of disease or a particular genetic trait.

Figure 2:
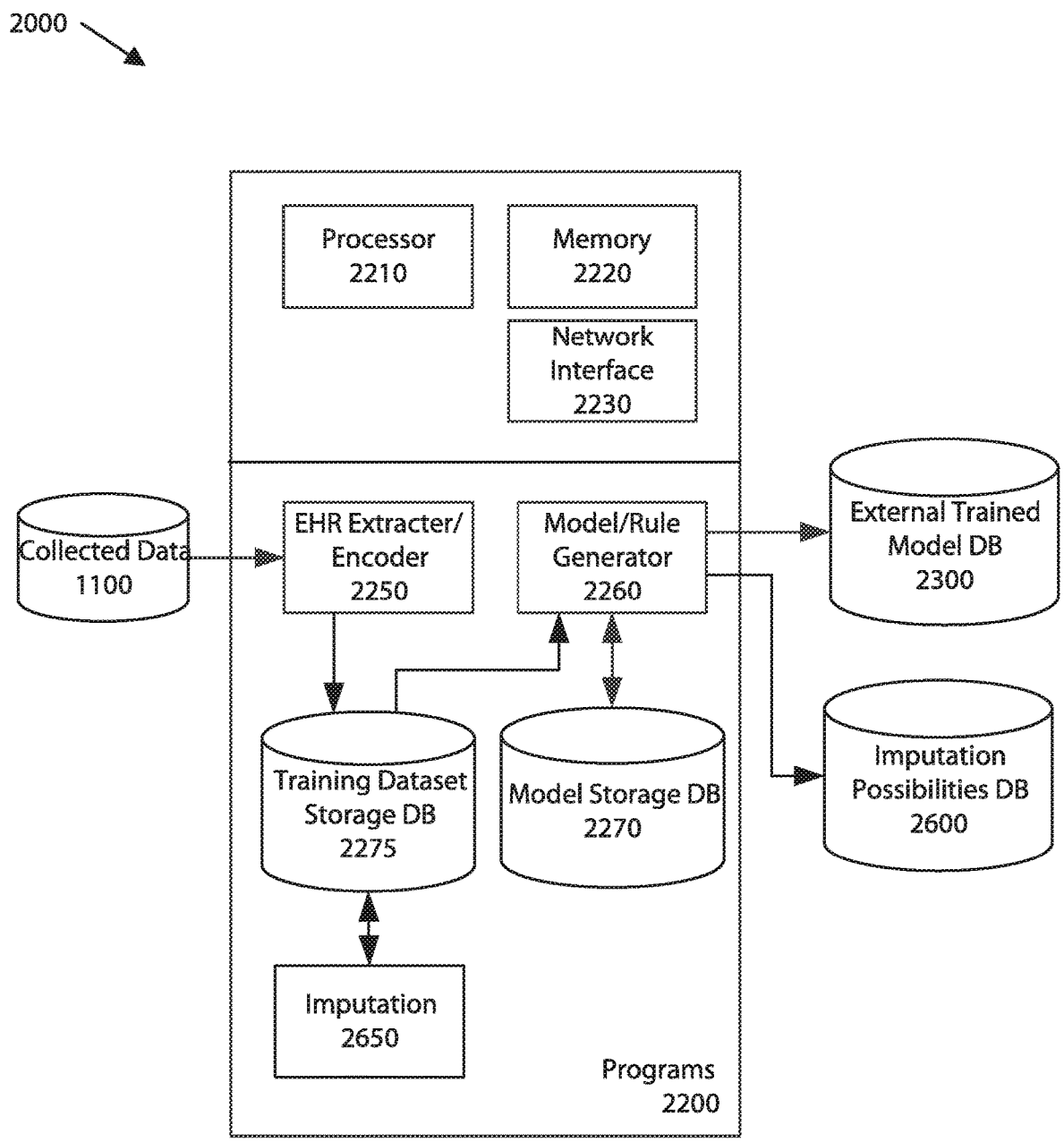
FIG. 2 illustrates an exemplary computer implementation of the training portion of the current technology.

The EHR data is mined (1200) for diagnosis (DX), treatment (RX), and outcome (end state, length of survival) information, and any additional data needed to create at least one collected dataset. The statistical significance data is used to select, from the collected dataset, genetic markers for inclusion in training datasets, based upon the usefulness of the genetic markers for determining diagnosis, treatment, and predicted outcomes, based in part on their p-value correlation values. Genetic data is optionally imputed by the training dataset imputation process (1220) with the collected dataset(s) to generate one or more processed collected dataset(s). The processed collected dataset(s) comprise collected and imputed genetic data that includes a more complete set of the selected genetic markers than the collected dataset(s) contains. The imputation process may be performed across all of the collected dataset(s), or may be performed limited on the basis of one or more of diagnosis and/or treatments identified in a collected dataset(s). The training dataset imputation process (1220) operates in a manner consistent with the steps described below for the imputation process (1650), and uses either (or both) trained models from the imputation model database (1300) and rules from the imputation possibilities database (2600). If imputation is not performed, the collected dataset is copied to the processed collected dataset. The processed collected dataset is stored in the training dataset storage database (FIG. 2, 2275).

The resulting collected dataset and/or one or more processed collected datasets are used to fully train (1250) one or more multi-task trained prediction models. The resulting trained models (e.g. models 1410*a*, 1410*b*, . . . ) are stored in a trained model database (1400), indexed by one or more of diagnosis, treatment, and genetic data. The trained models are used by the system to complete datasets by imputation (e.g. an imputation trained model), recommend treatment courses, and predict treatment outcomes.

Additional training process improvements involve producing one more trained models that identify imputation genetic information to be produced in patients' collected dataset when incomplete genetic information is discovered. In some embodiments, the training system uses one or more disease-specific or immunologic genetic profiles to determine a set of associated genetic information, where the profile identifies the genetic markers associated with a specific disease or immunologic states. The profiles may be implemented as associations between specific genetic information identified in a database. The training system uses a model/rule generation program (FIG. 2, 2260) to generate entries in an imputation possibilities database (2600) that includes one or more rule definitions identifying mapping of strengths of measured genetic values to imputed values of the generated genetic information. The training system model/rule generator (2260) also trains imputation models to determine genetic information missing from a patient collected dataset based on other information present in the patient collected dataset and training collected datasets (e.g. RX, DX, patient demographic data), and in some embodiments based on information in the imputation possibilities database, and stores the resulting imputation trained models (e.g. trained model 1310*a*, 1310*b*, . . . ) in an imputation model database (1300). The imputation trained models provide an imputation definition and are subsequently used to impute least one aspect of an individual patients' genetic information in a patient's collected dataset.

6.3.2 Data Flow for Exemplary Predictive Mode Operation

Figure 4:
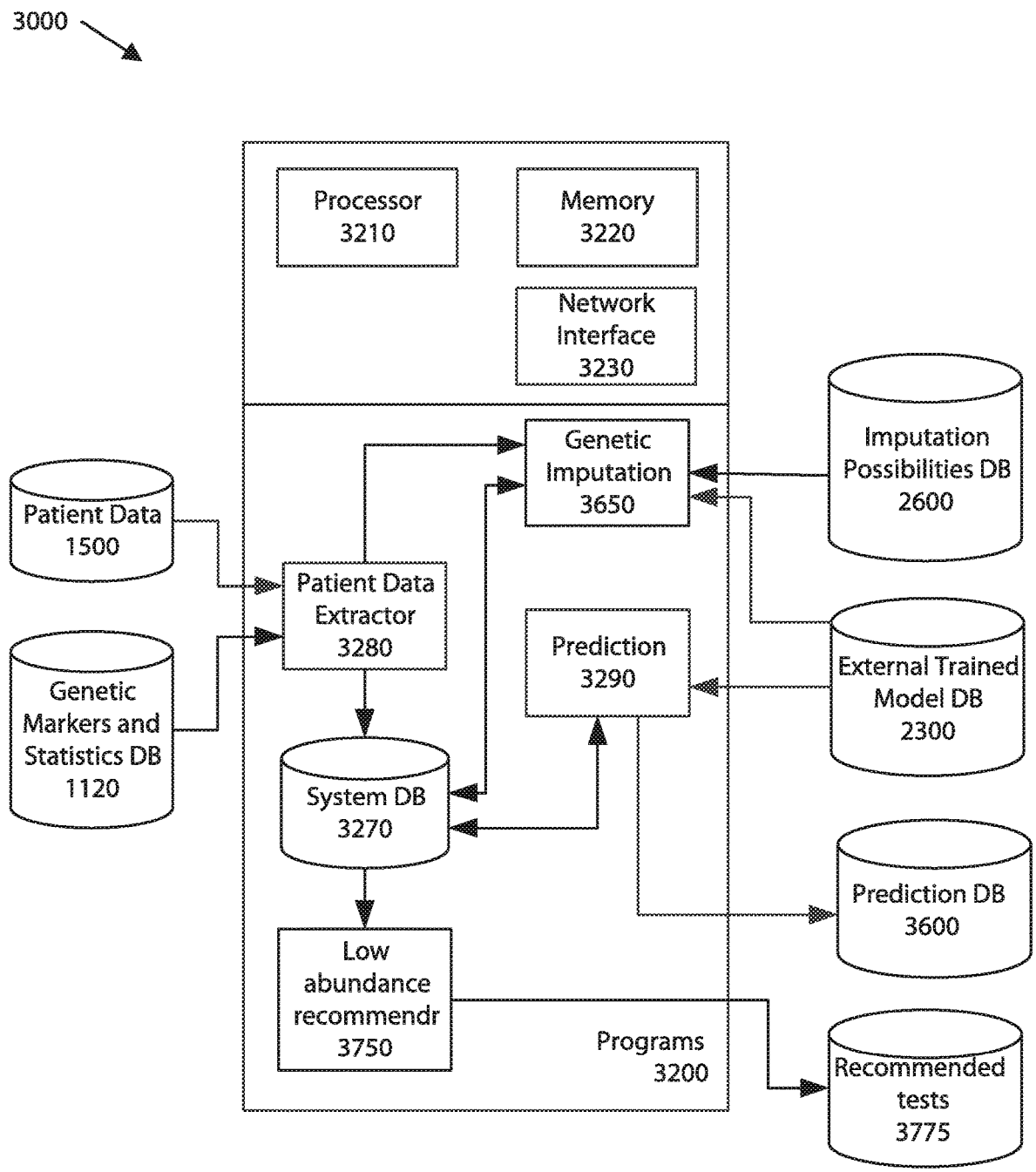
FIG. 4 illustrates an exemplary computer implementation of the training portion of the current technology.

After the trained model databases are constructed, the system operates in predictive mode by accepting patient-specific genetic and EHR data and replicating the previously described data mining operations to identify DX, RX, outcome (to date), and genetic data (e.g. tumor, VCF, and microbiome) associated with the patient and writes the data to the patient database (1500). This step is performed by the patient dataset extractors program (FIG. 4, 3280). The information collected is generally incomplete, as the patient is undergoing treatment or is being monitored post-treatment. The information associated with a particular patient is read from the patient collected dataset database (1500) and/or one or more EHR programs (not shown). These sources comprise one or more collected datasets and/or processed collected datasets associated with specific patients. Alternatively, some of the information may be read directly from genetic sequencing equipment and assay array readers (such as an Affymetrix GeneChip scanner not shown), and/or from other sources.

The patient's collected dataset(s) is then ordered on the basis of genetic information corresponding to one or more diagnoses or treatments. In one exemplary embodiment, the collected information is ordered by the most likely variant using the VCF SNP information (1600) (which is obtained from summary statistics, GWAS-like work, or other predictive models of immune and oncology-related traits) and the system proceeds to the imputation step (1650). The imputation step is provided by a genetic imputation program selecting and executing on a computer (e.g. imputation program FIG. 2, 2650 or FIG. 4, 3650). In some embodiments, the imputation program is shared across multiple imputation process sets and is called an imputation engine.

The genetic imputation program (or imputation engine) operates on the genetic information from one or more datasets (either patient's collected data or training collected data) in order to enhance the dataset(s) by imputing missing genetic data using one or more imputation trained models (taken from the above-mentioned imputation database 1300). Alternatively, or in addition, in some exemplary embodiments, rules stored in imputation possibilities database (2600) are used during imputation.

The process of imputing data completes missing or low expressed portions of the patient's genetic information. In some embodiments, the system limits imputation to specific genetic markers on the basis of information in the dataset, e.g. patient data such as RX, DX, demographic data, or specific genetic markers that are included in the database of genetic markers (which may by additionally identified as associated with specific type of patient data), genetic markers having a significance greater than a threshold value, or genetic markers that are associated with an identified disease, treatment, tumor, or immunological state. In an exemplary embodiment, the system limits imputation to missing genetic markers that have an associated with a disease identified in the patient's dataset. Alternatively, the limitation may be for imputations where the p-value of greater than a pre-determined and stored threshold value, for example, a threshold value greater than 75%, greater than 80%, or greater than 90%. The threshold value is associated with each set of selection parameters (such as RX, DX, specific demographic data) and is stored in a system configuration or database (not shown). The imputation process allows prediction models to be more accurate in their predictions by eliminating conditions in which insufficient distinguishing data is in the patient's records, by being able to utilize a wider set of features that have known association with the patient's particular condition, as well as in aggregating data sources from different datasets. The processed collected data (1675) is optionally logically associated with the patient's EHR data, and is passed, along with the patient's EHR data, to the prediction step.

The prediction step (1700) uses the trained prediction models from the prediction model database (1400) against the patient's processed collected dataset (1675) in order to establish or confirm a diagnosis, identify and recommend one or more treatments (RX) in ranked order of predicted effectiveness given the patient's processed collected data, and predict the outcomes of each treatment (survival, length, and end state).

The prediction step comprises selecting and executing a set of genome-specific trained models (1410a, 1410b, 1410c) each of which is trained to predict the effects of a particular gene in the input set of measured and imputed genes. Each genome-specific trained model predicts the outcome influenced by the particular gene in light of the DX and RX (e.g. the diagnosis and drug response).

The predicted outcomes generated by one or more genome-specific trained models are optionally combined to create a combined trained model (1415).

The combined trained model is created by training the model to predict the results of the combination of outcomes predicted for each of the genes represented by the individual genome-specific trained models. Based on a combination of outcomes predicted by multiple genome-specific trained models, the combined trained model generates a single trained model output that predicts one or more of the following: a disease diagnosis (DX), a treatment recommendation (RX), patient outcomes, and probabilities for each outcome. An exemplary combined trained model output includes one or more predicted outcomes based upon the combination of the determined genetic, DX, and RX information. Specifically, in some exemplary embodiments, the resulting combined trained model output includes prediction of a drug (RX) response based upon one or more genes identified as present in the collected and processed collected datasets. Exemplary combined trained model output includes one or more predicted outcomes, each with an associated outcome probability, and each based on a different treatment (RX) recommendation.

The two step prediction method of the technology described herein has a number of advantages over known prediction systems that may use a monolithic trained model to predict outcomes. For example, by selecting and executing first genome-specific trained models specific to certain genetic markers, the system saves computing resources by only reasoning over the all of the genetic markers using models that each include many less nodes or other model parameters than would be required for a monolithic model trained on a larger set of genetic markers. Further, the arrangement of multiple genome-specific trained models can be executed using parallel processing techniques, as are known to those having skill in the art, which may save time required to generate an outcome. In addition, training and prediction efficiency of the second model is improved by providing second model inputs that comprise information that has been reasoned over by the first, genome-specific, trained models rather than raw or unprocessed input data. In this manner, in an exemplary embodiment includes multiple genome-specific trained models that each pre-process collected genetic marker information in parallel to generate input features that are processed more efficiently by the second model as compared to known prediction models which distinguish undifferentiated data and thus must be trained with substantially larger training datasets.

6.3.3 Genomic Imputation

Genomic imputation, for example DNA Polymorphism (e.g., single nucleotide polymorphism (SNP)) imputation, is typically done for the whole genome at once without prioritizing specific regions in existing imputation methods. In contrast, imputation methods of the technologies are targeted to specific genetic information, i.e. genetic information that has been discovered to be statistically significant for predicting outcomes, generating probabilistic outcome measures, and for recommending treatments for specific diseases or immunological conditions, for example for specific tumor or cancer types.

Some exemplary configurations of the technologies described herein use an imputation method that is based on an LSTM autoencoder tuned to perform imputation on regions of interest that are prioritized by relevance to selected conditions or diseases of therapeutic interest. Other imputation methods may also be used as described below. Data mined from one or more data sources, such as the whole genome sequencing data of the thousand genomes project, UK Biobank, and more may be used for this purpose. Further, by leveraging summary statistics from GWASs (both public and private) that are oncology and immunology related, the imputation methods described herein prioritize SNPs that have significant p-values in those GWASs, thereby increasing specificity and accuracy for imputing the prioritized SNPs, including low abundance SNPs, and reducing computing resources by limiting the scope of imputation.

One aspect of the system is the imputation of missing SNPs for the construction of a shallow long short-term memory (LSTM) autoencoder for four inner layers (e.g. 6 layers overall). The input layer comprises the SNPs identified by particular assay arrays (e.g. from Illumina's MEGA array, or other arrays) and the output layer provides a complete genome of a target set of genes, for example the complete genome of the set of HLA-A and HLA-B genes. The four inner layers comprise two RNN layers and two convolution layers.

The various layers have selected weights (loss functions) selected as follows.

A set of SNPs (e.g. HLA SNPs) that are not part of the selected assay arrays, and weights associated with each SNP.

Parameters from Polygenic risk scores associated with auto-immune diseases.

Parameters from Polygenic risk scores associated with cancer pre-disposition.

Parameters identified in the literature (e.g. Stanford GWAS, literature searches).

In a first exemplary embodiment, trained models (1310a, 1301b, 1310c) each include a trained LSTM autoencoder. In a particular exemplary embodiment, each LSTM autoencoder is trained to impute genetic information corresponding to a particular disease state, immune state, or condition. For example, a first trained model (1310a) is trained using one or more GWASs corresponding to pancreatic cancer and second trained model (1310b) is trained using GWASs corresponding to breast cancer. When trained in this way, the trained models may impute genetic information differently due to changes the underlying disease or changes in the disease state, immune state, or condition, which improve the overall accuracy of the results. When performing imputation, the system selects, from the imputation model database (1300), one or more of trained models (1310a, 1310b, and 1310c) for use in imputing genetic information that corresponds to a particular disease or condition of interest. In this manner, the system saves computing resources by only imputing genetic information that is associated with the disease or conditions of interest and increases accuracy of the imputations performed as compared to existing imputation methods.

In a second exemplary embodiment, the system includes one or more imputation possibilities databases (2600), each with multiple imputation rule entries. The imputation possibilities database(s) may be stored in a single database, or alternatively, may be stored in multiple databases to segregate imputation rules created for use by a specific source and/or for a specific purpose, e.g. for use with a specific diagnosis. In an exemplary embodiment, at least some of the multiple entries of the database are generated from or by one or more trained machine learning models. In an alternative embodiment, one or more of the entries in the database(s) are generated and entered into the database externally to the system.

Each entry in a imputation possibilities database includes at least one measured genetic trait, for example a measured SNP, one or more imputation possibilities corresponding to the measured trait, and, in some embodiments, one or more rules for selecting an imputation possibility for inclusion with imputed genetic information.

The system creates, updates, adds, and deletes entries to the imputation possibilities database based on newly processed patient EHR information during a training process. In this manner, the system continuously improves the accuracy of produced imputations as the machine learning models are trained.

An exemplary imputation rule is shown in three-part form,
 an evaluation expression specification used to determine the presence of conditions for imputation,
 an imputation action, and
 a set of imputations.

The evaluation expression specification is a Boolean expression that is evaluated by the imputation rule execution function (part of the imputation program) against a collected dataset and/or processed collected dataset in order to determine a true/false result on whether the imputation action is to be selected and applied to modify the resulting processed collected dataset. The expression is evaluated; if true, imputation is selected and applied, if false, imputation is not performed. Any expression language may be used for the specification of the expression, as long as arbitrarily large sets may be specified.

Expression Example Syntax

An example expression definition may be encoded using a grammar, such as the example below in Backus normal form (BNF):

Expr::={NOT}<gene ID>{<relop><value>} {AND|OR <expr>}+

Relop:=~|<|=|>|>=|<=

Value:=<number, magnitude of expression>|in <gene class/subclass ID>

A non-exhaustive exemplary list of Gene ID's usable by the invention is included in Table 1.

Gene class/subclass ID's are understood in the art. The IN operator treats the class/subclass as a set, and tests for a particular gene being a member of that set.

TABLE 1

| Gene ID | Gene ID | Gene ID | Gene ID | Gene ID | Gene ID |
|---|---|---|---|---|---|
| CXCR5 | KLRF1 | TBX21 | MS4A1 | VPREB3 | GATA3 |
| ASB2 | GNLY | IL12RB2 | CD79A | PAX5 | IL4 |
| CD200 | LILRB1 | TRBV25-1 | CD79B | LILRA4 | IL5 |
| BCL6 | CCL4 | TRAV10 | HLA-DOB | IL3RA | IL13 |
| PDCD1 | NKG7 | ZBTB16 | BANK1 | CLEC4C | IL17RB |
| CD4 | FCGR3A | CD33 | JCHAIN | LAMP5 | CCR4 |
| IL17A | KLRD1 | CD14 | IGHM | PTCRA | IL9R |
| IL17F | CD244 | TGFB1 | IGKC | TNFRSF21 | TNFSF10 |
| IL22 | SLAMF7 | CD3D | IGHA1 | FUT7 | IL11RA |
| KIT | PRF1 | CD3G | IGHG2 | ITGA2B | TNFRSF9 |
| IL17RE | F2R | CD3E | IGHD | ITGB3 | TIGIT |
| RORC | KLRK1 | TRAC | CR2 | CXCL5 | ICOS |
| CTSH | CTSW | TRBC2 | TNFRSF17 | S100A8 | IL2RA |
| LGALS3 | CCL5 | TRBC1 | TNFRSF13B | LYZ | TOX |
| CCR6 | CST7 | IL7R | TNFRSF13C | S100A12 | CCR10 |
| TNFSF13B | TGFBR3 | CD2 | BLK | FCN1 | CCL27 |
| TNFRSF18 | CD300A | TCF7 | FCRLA | MNDA | CCR8 |
| IL1R1 | IL5RA | LEF1 | CD22 | CTSS | CTLA4 |
| CX3CR1 | GZMA | CD27 | FCER2 | MS4A6A | DUSP4 |
| ZEB2 | IL18RAP | CD8A | PDLIM1 | CST3 | FOXP3 |
| ITGAM | KLRG1 | CD8B | POU2AF1 | CSTA | IKZF2 |
| EOMES | GZMK | TRGV2 | TCL1A | CYBB | LRRC32 |
| FCRL6 | CXCR3 | IL32 | CD40 | NCF2 | IL2 |
| GZMH | CCR5 | CD6 | AFF3 | AIF1 | IL20RA |
| GZMB | IFI27 | CD19 | BLNK | CFD | IL21 |
| ITGB1 | SMAD3 | FOXJ1 | ILDR1 | IL37 | HLA-DQB2 |
| CCR7 | IL2RB | IGHG4 | TRAV1-2 | NR1I2 | LAYN |
| SELL | KLRB1 | IGHG1 | CCR1 | CSF2 | TNFSF15 |
| FCER1G | MAP3K1 | IGHA2 | LTK | LIF | CCL7 |
| FCGBP | KIR2DL3 | XBP1 | IL23R | XCL1 | CST6 |
| ENTPD1 | KLRC3 | IGHJ2 | FLT4 | TNFSF11 | CCL13 |
| HAVCR2 | KLRC2 | CD38 | IL4I1 | TXK | CCL8 |
| CXCL13 | KIR3DL1 | IGLC1 | CXCR6 | CD7 | CXCL11 |
| LAG3 | KIR2DL4 | IGHJ1 | NCR3 | CRTAM | CLEC4D |
| PRDM1 | KIR2DL1 | TCL1B | CCL20 | FCER1A | CCL2 |
| IL6ST | CD160 | IL21R | CCR2 | ENHO | CD93 |
| TNFRSF10D | EGR1 | IL4R | TRGC1 | CD1C | CLEC4E |

TABLE 1-continued

| Gene ID | Gene ID | Gene ID | Gene ID | Gene ID | Gene ID |
|---------|---------|---------|---------|---------|---------|
| IRF4 | KIR3DL2 | TGFA | CCL4L2 | CD1E | FCGR1A |
| FAS | CD63 | TRDV2 | PDGFRB | IDO1 | FCGR1B |
| CD58 | ITGA1 | TRDV3 | FCGR2A | CD200R1 | CCL19 |
| SLAMF1 | CCR9 | TRDC | XCL2 | FLT3 | CCL24 |
| NCR1 | CXCR1 | KLRC1 | TRGV4 | XCR1 | CCL26 |
| BACH2 | NCAM1 | ITGAX | FCGR2B | HLA-DQA1 | CXCL12 |
| CD9 | CCL3 | TRGV9 | LYN | HLA-DQB1 | C1QA |
| CD70 | CXCR2 | C1QC | TRGC2 | CD1B | C1QB |
| EBI3 | IL7 | MSR1 | CLEC4F | CD109 | MS4A7 |
| CD80 | FCGR3B | ICAM4 | FCRL1 | CXCL14 | C3 |
| CD44 | FGFBP2 | LTB | ITGAL | HLA-DRB1 | GPR183 |
| ADGRG1 | | | | | |

Examples of evaluation expression specifications include the following. The expression is evaluated; if true, imputation is selected and applied, if false, imputation is not performed.

Presence of a genetic marker or set of genetic markers, e.g. {M} or {M, M'}.

Presence of a set of genetic markers {M} and the absence of genetic marker {M'}.

Presence of a genetic marker with an expression level above a specified threshold (e.g. {[M, >threshold value]}, where [M, threshold value] represents M the genetic marker, and threshold value is a measured value of the expression of M).

Presence of a genetic marker with an expression level below a specified threshold (e.g. {[M, <threshold value]}, where [M, threshold value] represents M the genetic marker, and threshold value is a measured value of the expression of M).

Presence of a genetic marker with an expression level equal to a specified threshold (e.g. {[M, =threshold value]}, where [M, threshold value] represents M the genetic marker, and threshold value is a measured value of the expression of M).

Presence of a genetic marker with an expression level between two specified thresholds (e.g. {[M, >=threshold 1, <=threshold 2] }).

Other expression operators may be added without departing from the scope of the present technology.

The imputation action is a code that indicates how the imputation process should process the information, selected from a list including:

Add—Add the imputations/outcomes data specified to the resulting processed collected dataset.

Remove—Remove the imputations/outcomes data specified from the resulting processed collected dataset (if present)

Modify—Modify existing data in the processed collected dataset in accordance with the imputations/outcomes data.

Modify-relative—Modify existing data in the processed collected dataset in accordance with the imputations/outcomes data by adjusting the reported expression level values (but not changing the reported genetic markers) as a function of one or more gene expression levels. For example, increment/decrement an expression level, or set an expression level to a percentage of another gene's expression level.

Other actions may be added to the system within the scope of the technology.

Exemplary imputation rules include:

Given an evaluated Boolean result value of "true" for expression X, where X represents an expression as described above, impute and add a set of genes {Y', Y'', Y''', . . . } with an imputed strength of expression of each gene in the imputed set.

Given an evaluated Boolean result value of "true" for expression X, impute and add genetic data represented by Y', with a corresponding imputed strength of expression that is a function of the measured strength of expression of one or more elements used as parameters of X.

Given an evaluated Boolean result value of "true" for expression X, add a set of genetic information {e.g. Y', Y''} and corresponding imputed strengths of expression.

Given an evaluated Boolean result value of "true" for expression X, where X includes the testing measured genes X' and X'', add a set of genetic information {Y', Y'', Y''' } with specified levels of expression.

Given an evaluated Boolean result value of "true" for expression X, where X includes the testing of measured gene X' with an expression level of less than a specified value, modify the specified expression level of X' to a specified value.

Given an evaluated Boolean result value of "true" for expression X, where X includes the testing of measured gene X' with a measured expression level of less than a specified value, modify-relative the specified expression level of X' by altering the specified expression level of X' by a function related to the measured expression level (e.g. changing the measured expression level value by a calculated amount or percentage).

Given an evaluated Boolean result value of "true" for expression X, modify-relative the strength of expression of a gene X' by setting the strength of expression of X' as a function of the strength or certainty of an imputation link between an element of X and X' (e.g., based upon the strength of linkage of SNPs to a particular disease or disorder).

Given an evaluated Boolean result value of "true" for expression X, impute and add a set of genetic information {Y', Y'', Y'''} and based upon the imputed genetic information Y', further impute genetic information Z', which is related to Y', to produce the set of imputed genetic information {Y', Y'', Y''', Z'}.

Given an evaluated Boolean result value of "true" for expression X, impute by deleting the set of genetic information {Y', Y'', Y''' }.

Further exemplary rules can specify imputation strength scores as a function of one or more additional or alternative factors that may influence imputation accuracy including, for example, SNP density and sequencing depth or coverage.

In a first exemplary embodiment, the system uses the generic information extracted from the collected dataset to measured genetic traits contained in one or more instances of imputation possibilities database(s) (2600) and uses the associated rules to determine imputed genetic traits based on the measured genetic traits and RX/DX information in the collected dataset.

In a second exemplary embodiment, one or more of the trained models (1310a, 1310b, and 1310c) compares genetic information extracted from the collected dataset to measured genetic traits contained in one or more instances of genetic possibilities database(s) (2600) and uses the associated rules to determine imputed genetic traits based on the measured genetic traits. In an exemplary embodiment, the trained model(s) can function as expert systems modules by identifying and implementing only those rules contained in the imputation possibilities database necessary to produce imputed genetic information based on the observed genetic information (e.g. gene IDs such as those examples enumerated in Table 1) and a newly identified RX or DX value generated by the trained model. In this manner, the system can generate imputation results using fewer computing resources as compared to traditional imputation methods and programs.

In some exemplary embodiments, the system uses one or more additional or alternative methods to impute genetic information based on measured genes including, for example, Bayesian approaches and graphical causal models.

6.3.4 Low Expressed Genetic Information

Some exemplary genetic markers include low expressed genetic information, for example low abundance markers, e.g., rare SNPs or other rare variants. "Low expressed genetic information" is defined herein as genetic information which may be difficult to characterize by a default or usual sequencing depth or coverage used by the system. Low expressed genetic information may also be difficult to characterize by imputation, for example due to low levels of association or linkage with other markers that are more readily observed. In an exemplary embodiment, the system parses a patient EHR dataset and determines genetic markers contained therein, for example genetic markers determined by a low coverage or low depth, e.g. 4× or 8×, sequencing performed on one or more biological samples (blood cells, tumor cells, etc.) from the patient. The system determines whether genetic markers are missing from the initial sequencing results, i.e. from the observed genetic markers, and, if so, uses one or more of the imputation methods of the exemplary technology described herein to attempt to impute the missing genetic markers, which can include low abundance genetic markers. Because the imputation methods are designed to specifically impute specific genetic markers, as previously described, low abundance genetic markers are more readily and accurately identified by the imputation methods.

If, however, the system determines that one or more low abundance genetic markers have not been observed, and that their values have not been successfully imputed, the system can recommend (using a recommender program like the low abundance method recommender program FIG. 4, 3750) further tests to characterize the low abundance markers, for example by performing deeper and/or targeted sequencing on the one or more biological samples that were previously studied or from one or more biological samples newly acquired from the patient. In a particular embodiment, the recommender system includes a database of methods for generating additional genetic data. In an exemplary embodiment, the database of methods for generating genetic data includes, for example, one or more of amplification methods, sequencing workflows, and targeted assays that may be recommended as defined in the recommended tests database (3775). The system selects from the database one or more methods for generating genetic data specific to the one or more missing or low abundance genetic markers. For example, the system selects an amplification method targeted for a particular low abundance genetic marker in order to obtain new data to complete the collected data. The system then recommends performing the selected methods/procedures for generating genetic data on one or biological samples from the patient.

6.3.5 Exemplary System Architecture

FIG. 2 illustrates an exemplary computer system (2000) of standard manufacture that provides and implements one embodiment of the training aspects of the described system. An exemplary computer system comprises one or more processors (2210), persistent and transient memories for storing data and programs (collectively 2220), storage access circuitry that enables the processor to read and write data and programs from and to the memories, and one or more network or other communications interface(s) (collectively 2230) (e.g. an Ethernet, 802.11, cellular radio transceiver, and direct hardware interface operably connected to external databases comprising training datasets and trained model databases). An exemplary computer system further comprises, in at least one of its persistent memories, one or more programs (collectively 2200), which may include specialized programs to implement collected dataset processing (e.g. extractor/encoder 2250), genetic information imputation (e.g. imputation program 2650), and trained model and rule generation (e.g. model/rule generator 2260) as described herein.

EHR extractor/encoder program (2250) receives, from collected data database (1100), historical patient EHRs, e.g., EHRs from a cohort of patients comprising a particular patient population of interest, and mines the patient EHRs datasets in order to generate datasets including DX, RX, outcomes, and genetic data associated with the EHRs data, which is stored in training dataset storage database (2275).

The imputation program (2650) receives, from training dataset storage database (2275), collected data including genetic information comprising one or more of measured patient RNA, DNA, and microbiome genetic data and uses one or more imputation methods to produce processed collected data that includes imputed genetic information values. In an exemplary embodiment the imputation program produces genetic markers associated with genetic markers identified for imputation, as defined herein. The imputation program stores processed collected data, including imputed values of genetic information, in the training data storage database.

Model/rule generator program (2260) receives, from training dataset storage database (2275), collected and/or processed collected data including genetic information and other patient-related data (e.g., DX, RX, outcomes). In a first exemplary embodiment, the model/rule generator program receives, from model storage database (2270) one or more untrained models. The model/rule generator program uses the collected and/or processed collected data to train the untrained models, thereby generating trained imputation models (e.g., 1310a, 1310b, 1310c) which it stores in the external trained model database (2300). In a second exemplary embodiment, the model/rule generator program uses the collected and/or processed collected data to generate one or more imputation rules, which it stores in imputation possibilities database (2600).

The computer system may optionally further comprise one or more database((s)/cache(s) (e.g. databases 2270, 2275) in which the computer stores information about one or more of collected data, processed collected data, training datasets, and trained models with which it is configured to inter-operate. The database/cache may be stored in an internal memory of the computer system (e.g. model storage database 2270, training dataset storage database 2275) or may be stored in an external database such as the collected dataset database (1100), the trained model database (2300), or the imputation possibilities database (2600) to which the system is operably connected. In some embodiments, the computer system may further comprise a secure key storage mechanism (not shown) such as a secure processor, a TPC chip, or other mechanism in which it stores cryptographic materials that protect patient confidential information.

When operating, the exemplary computer processor executes one or more of the exemplary systems' programs from persistent or transient memory in order to convert the general purpose computer into a processor-controlled role-specific device that implements the one or more defined processes of the executing programs.

Figure 3:
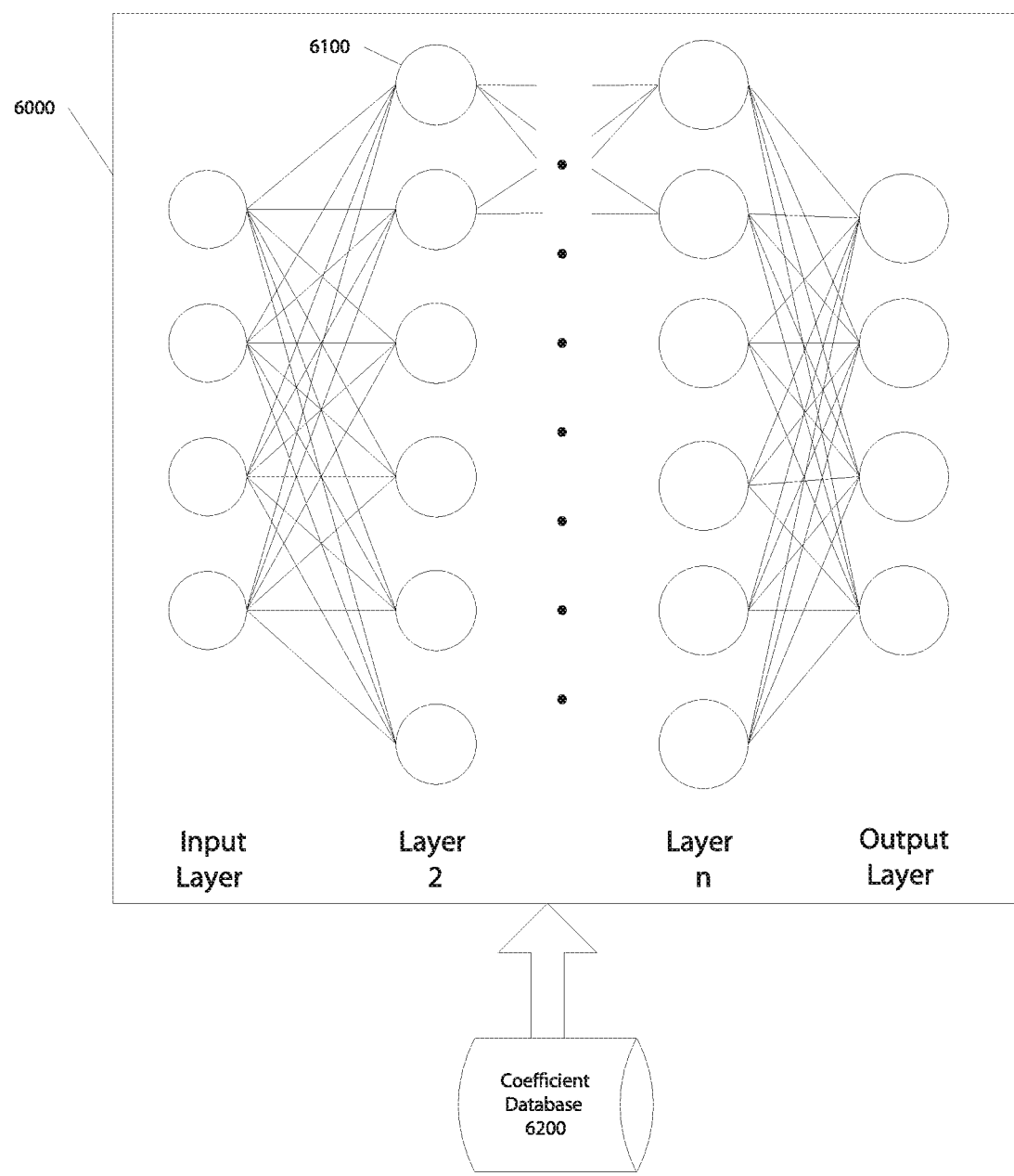
FIG. 3 illustrates an exemplary computer implementation of a neural network coupled to a coefficient database.

FIG. 3 illustrates an exemplary deep neural network engine (6000) using configurable coefficient storage in the form of a coefficient database (6200). When combined within an exemplary computer system (e.g. system 3000 described below), the neural network engine is configured by the processor by selecting coefficients (6100) read from a coefficient database and populating the neural network with those coefficients. Exemplary coefficients comprise parameters including weights and biases associated with individual neurons or blocks of a particular neural network configuration and in some embodiments include specification of one or more of activation functions and transfer functions. The neural network engine may be implemented as stand-alone computer hardware system, or as a module within a larger computer system without deviating from the scope of the present technology. The neural network engine may include neural network configurations of differing types. In an exemplary embodiment, the neural network engine includes a feed forward neural network, for example a feed forward back propagation neural network. In further embodiments the network engine includes one or more additional or alternative neural network configurations, alone or in combination, including, but not limited to, recurrent neural networks (RNN), for example long short term memory (LSTM) RNN, convolutional neural network (CNN), Bayesian or Belief neural network (BNN), or other directed acyclic graph configuration of a neural network. In some exemplary embodiments, the neural network engine includes a neural network configuration having multiple hidden layers of differing types, for example one or more RNN layers and one or more CNN layers.

FIG. 4 illustrates an exemplary computer system (3000) of standard manufacture that provides and implements one embodiment of the predictive aspects of the described system. An exemplary computer system comprises one or more processors (3210), persistent and transient memories for storing data (collectively 3220), storage access circuitry that enables the processor to read and write data and programs from and to the memories, and one or more network or other communications interface(s) (collectively 3230) (e.g. an Ethernet, 802.11, cellular radio transceiver, and direct hardware interface operably connected to external databases comprising patient EHR data and trained model databases). An exemplary computer system further comprises, in at least one of its persistent memories, one or more programs (collectively 3200), which may include specialized programs to implement dataset collection and extraction (e.g. patient data/extractor program 3280)), imputation (e.g., genetic imputation program 3650, a set of recommender programs (e.g. low abundance method recommender program 3750), and treatment/outcome prediction (e.g. prediction program 3290) as described herein.

Patient data extractor program (3280) receives, from patient data database (1500), collected data corresponding to a selected patient. In some embodiments (not shown), the patient data extractor receives data directly from an EHR, and/or directly from a genetic reader. When new data is obtained, the patient data extractor program writes the collected data to the patient data database (1500). The patient data extractor program then mines the patient's collected dataset to identify aspects of the collected data including DX, RX, outcomes, and collected genetic data. In some embodiments, the patient data extractor program receives additional information identifying selected genetic markers (and/or genetic profiles) from a genetic markers database (1120) and limits the collected genetic data to include only those identified genetic markers. In additional exemplary embodiments, the patient data extractor program encodes the collected data for use by the system, for example, by standardizing aspects of the collected data by converting numerical laboratory test results to standardized ranges (e.g., low, normal, high). The patient data extractor program stores the collected data in system database (3270) or back to the patient data database (1500). In some embodiments, the patient data extractor program provides the collected genetic data directly to the genetic imputation program (3650).

Genetic imputation program (3650) receives collected genetic information from either the patient data extractor program (3208), system database (3270), or both and produces imputed values of one or more genetic data in the dataset as processed collected data, for example, creating genetic marker values and expression levels, that is missing from the collected data. In a first exemplary embodiment, the genetic imputation program retrieves, from external trained model database (2300), a trained imputation model and uses the trained imputation model to produce the imputed genetic information. In a second exemplary embodiment, the genetic imputation program retrieves, from imputation possibilities database (2600) one or more imputation rules and uses the one or more imputation rules to produce the imputed genetic information. The genetic imputation program stores the processed collected data, including imputed genetic information, in system database (3270) or in the patient data database (1500).

In some exemplary embodiments, the low abundance recommender program (3750) retrieves, from system database (3270) or the patient data database (1500), collected and processed collected data and determines genetic information including expression levels of one or more retrieved genetic markers that require imputation to create, modify, or removes information from either the collected and processed collected data. In some implementations, the system automatically selects one or more imputation steps to be performed. In other cases, the low abundance recommender program (3750) generates one or more recommendations for additional tests that may be run to create the missing genetic information and stores these recommendations in recommended tests database (3775). In some implementations, the recommendations may be produced in a form of a prescription that is subsequently made available to a testing provider, or is presented on an output device.

Prediction program (3290) receives, from system database (3270), one or more of collected and processed collected data and receives, from external trained model database (2300), one or more trained prediction models. The prediction program (3290) uses the one or more trained prediction models to generate, based on the collected and processed collected data, one or more predicted outcomes including, for example, DX, RX, outcomes, and projected survival duration. The prediction program (3290) stores the predictions in prediction database (3600).

In some embodiments, the prediction program compares successively generated stored predictions to subsequent predictions and outcomes to identify those cases where earlier predictions were not accurate. Those prediction cases where the prediction is less accurate than a specified threshold (stored in a configuration) and the underlying patient dataset may be copied to a collected data database (1100) for use in producing new iterations of trained models.

The computer system may optionally further comprise a local instance of one or more system database/cache (3270) in which the computer stores information about one or more patient data and trained models with which it is configured to inter-operate. The database/cache (3270) may be stored in an internal memory of the computer system (not shown) or may be stored in an external database such as the patient database (1500), the genetic markers and statistics database (1120), the trained model database (2300), the prediction database (3600), the recommended tests database (3775), and the imputation possibilities database (2600) to which the system is operably connected. In some embodiments, the computer system may further comprise a secure key storage mechanism (not shown) such as a secure processor, a TPC chip, or other mechanism in which it stores cryptographic materials that protect patient confidential information.

When operating, the exemplary computer processor executes one or more of the exemplary systems' programs from persistent or transient memory in order to convert the general purpose computer into a processor-controlled role-specific device that implements the one or more defined processes of the executing programs.

Figure 5:
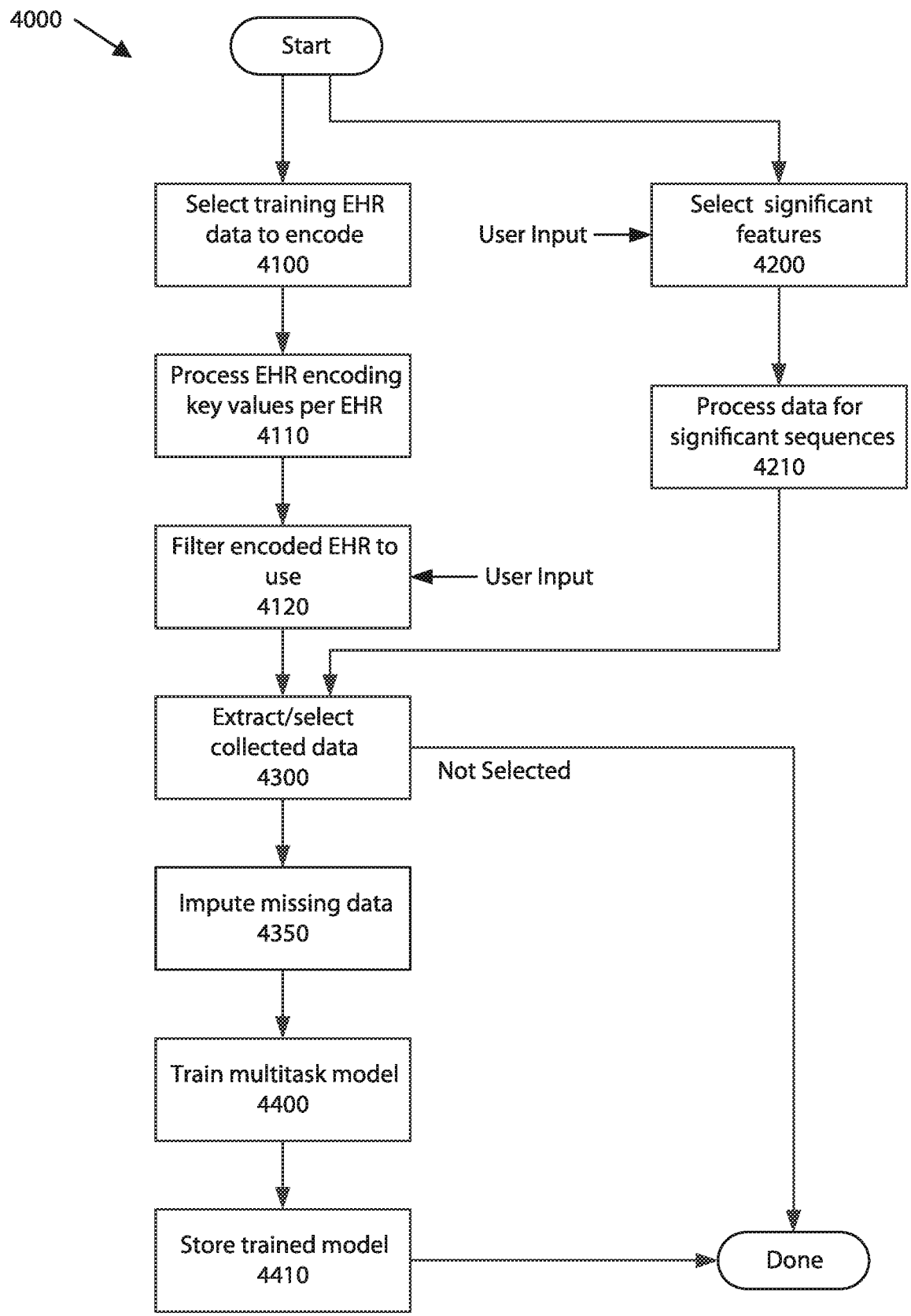
FIG. 5 illustrates an exemplary process flow for the training portion of the current technology.

FIG. 5 illustrates an exemplary process (4000) performed by the programs of the training computer system. The training system has two paths, one for training the multitask model and one for establishing the database of prioritized features (per the aforementioned GWAS and other private studies) used by the system. On the path for establishing the database of features, in step 4200, the user first selects significant features for a specific DX from the known literature and databases of summary statistics information. In step 4210, the system then processes the data in order to extract significant genetic sequences and associate these sequences with the DX and statistical significance of the sequences. The processed information is then provided to the training system for training the multitask model, and may be optionally stored in a database (step not shown) for later reuse.

On the path for training the multi-task model, in step 4100, the system selects one or more training datasets from either the collected data database (1100) or a training data storage database (2275) to encode/process. The selection may be on the basis of one or more identified DX, RX, outcomes, or on the basis of other factors determined by the user. In step 4110, the training dataset(s) are then processed, extracting and encoding the features needed to train a predictive model according to the technologies described herein. The extraction and encoding may include DX, RX, outcome, and genetic marker extraction and encoding.

In step 4120, the resulting training dataset is then filtered based upon user input to exclude anomalous data, and the resulting filtered training dataset is combined with the processed statistical significance information from step 4210 to produce a combined training dataset.

In step 4300, the combined training dataset is then down-selected on the basis of the identified genetic information present. The down-selection process identifies the information in the combined training dataset that will be useful in training a multi-task model for a selected DX/RX/genetic pair. If no data is selected, the current training session ends.

If there are training dataset(s) associated with to the specific training activity, the system selects those training dataset(s) and proceeds to step 4350 where it performs imputation steps to produce imputed values from among the genetic information identified in step 4300 as useful for training the multi-task model. The system performs the imputation using previously generated imputation trained models. Alternatively, the system may select an imputation possibilities dataset which may select and use imputation rules from the selected dataset in the imputation process.

The system then proceeds to step 4400, where it creates a trained model for the specific DX/RX/genetic pair using the selected elements of the combined training dataset. In step 4402, the system determines whether the multitask model has been optimized, for example by generating predictions using the model and labeled testing data, calculating a cost function based on comparison of the generated predictions and the testing data labels, and determining whether the cost function has been minimized. If the system determines that the model has not been optimized, in some embodiments it proceeds to step 4405 to update imputation models and/or imputation rules. The system then repeats imputation step 4350 and to produce new imputation results performs additional training on the multitask model using training data including the new imputation results.

If the system determines, at step 4402, that the multitask model has been optimized, it proceeds to step 4410 and the resulting trained model is then stored in a database such as the trained model database (2300), following which the training process completes. The training process may be repeated as often as necessary as new training dataset(s) or useful statistical significance data is made available, or when a new trained model is desired for a different DX/RX/genetic pair.

Figure 6:
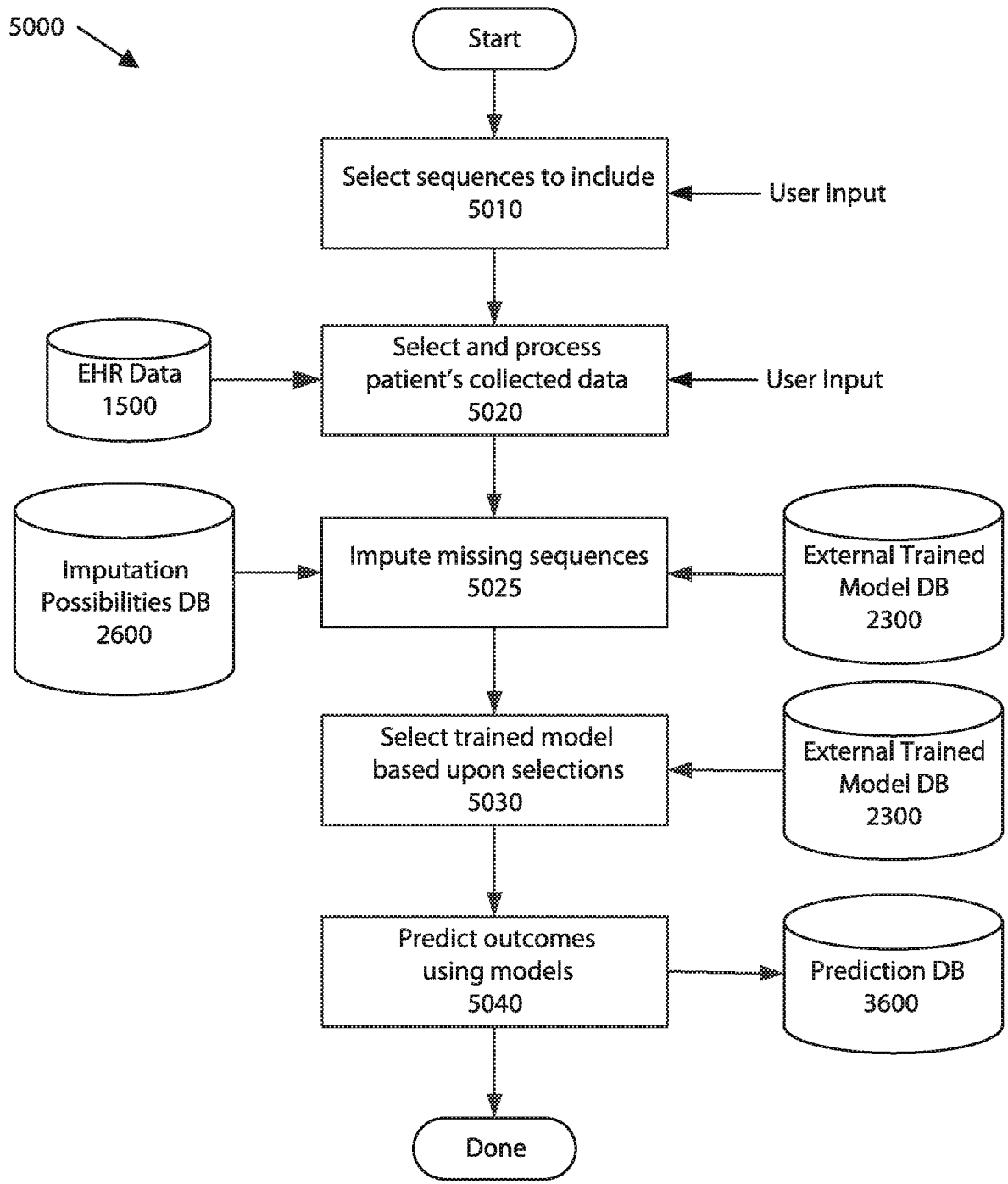
FIG. 6 illustrates an exemplary process flow for the diagnostic use of the current technology.

FIG. 6 illustrates an exemplary process (5000) performed by the programs of the predictive computer system.

The process starts with step S010, where the user selects genetic sequences to include in the prediction.

In step S020, the system processes the patient's collected dataset from the patient database (1500), selecting and extracting, on the basis of user input, the patient's DX, RX, treatment stage/outcome(s) to date, one or more collected datasets (e.g., VCFs), and, in some exemplary embodiments, microbiome features, e.g., alpha or beta diversity). User inputs may include the following:

User selection of results as absolute or relative survival curves.

User selection prioritizing or omitting different genetic features.

User option to manually enter clinical information (i.e. single gene mutations).

At step S025, the system performs any imputation necessary (1650 of FIG. 1) to adjust the collected dataset using one or more of the imputation trained models (e.g. 1310a, 1310b of FIG. 1). Imputation is used to enhance the patient's collected dataset (e.g. EHR data or directly read genetic data) by adding imputed values for missing information, thereby producing a processed collected dataset (e.g. 1675 of FIG. 1).

This permits the user to have control over the types of information used by the trained models. The selected information is then used to select one or more trained models (e.g. 1410a, 1410b of FIG. 1) from the trained model database (2300) in step S030.

In step S040, the selected trained model(s) are used to predict the outcomes based upon specific treatments and based upon at least some of collected data and/or processed collected data, including collected and, in some cases, imputed genetic information (1700 of FIG. 1).

In a particular exemplary embodiment, the system uses one or more selected trained models to generate multiple predicted outcomes, each corresponding to a specific treatment, thereby generating a set of treatment and predicted outcome pairs. The system further uses the trained models to generate a likelihood or probability metric associated with each of the predicted outcome/treatment pair and generates a ranked list comprising treatment/predicted outcome pairs, ordered according to the predicted outcomes and their probability metrics. The system then generates one or more treatment recommendations based on the ranked list. In an exemplary use case, the system uses the selected trained models to generate, for a particular cancer, predicted outcomes of up to four different treatments and a probability metric associated with each predicted outcome.

The selected trained models also operate as a recommender engine and produce one or more recommended treatments, in addition to predicting outcome, survival, and disease progression milestones and disease progression timelines. In an exemplary embodiment, the system uses the predicted outcomes to generate one or more treatment recommendations. The system may filter the predicted outcomes to eliminate any predicted poor outcomes, for example patient death or non-response. In one exemplary embodiment, the one or more treatment recommendations may include each treatment that was not associated with a poor outcome. In another exemplary embodiment, the one or more treatment recommendations include recommendations selected based on one or more additional criteria, for example treatments associated with a probability metric have a value greater than a threshold value or a the top treatments on a list of treatments ranked by probability metric values, e.g. the top two treatments or the top three treatments. These outcome predictions and treatment recommendations (combined model 1415 of FIG. 1) are stored in prediction database (3600) for subsequent use and comparison if the patient is re-processed using the system, for example the patient's EHR is updated with newly collected data at a subsequent time point.

In an exemplary embodiment, when newly collected patient outcome data is added to a patient's EHR, the system retrieves from the prediction database any predicted outcomes previously generated by the system and compares the newly collected outcome data to the previously predicted outcomes. If the newly collected outcome data does not agree with the previously predicted outcomes, the system may retrain the model(s) used to generate the outcome(s) or use one or more known reinforcement learning methods to update the trained models.

The system may also generate recommendations for additional testing to be performed. For example, the system may recommend additional testing to generate missing values of low abundance data that it is unable to generate using imputation methods of the technology, as described herein.

If the system produced one or more recommended treatments and/or recommended additional testing, a user of the system may take actions based upon the recommendation to convert one or more recommendations into a prescription/testing order for the identified additional tests and/or treatments. Referring back to FIG. 1, the system provides for an optional feedback loop in which the stored outcome predictions are compared against one or more subsequent patient state information (e.g. updated RX, DX information) and the accuracy of the prediction assessed. The prediction accuracy may be used to increase and decrease internal weightings in the predictive models used to make the predictions.

Similarly, by using RX and DX data compared against the outcome predictions, the system may provide an assessment of the current progression of the patient's disease in relation to the predicted disease progression predictions. Updated predictions may also be made on the basis of this assessment.

6.4 Conclusions

It will also be recognized by those skilled in the art that, while the technology has been described above in terms of exemplary embodiments, it is not limited thereto. Various features and aspects of the above described technology may be used individually, jointly or in combination. Further, although the technology has been described in the context of its implementation in a particular environment(s), and for particular application(s), those skilled in the art will recognize that its usefulness is not limited thereto and that the present technology can be beneficially utilized in any number of environments and implementations where it is desirable to provide a highly accurate treatment recommender and condition monitoring system or other implementations. Accordingly, the claims set forth below should be construed in view of the full breadth and spirit of the technology as disclosed herein.

What is claimed:

1. A system for variably imputing genetic information into a genetic data set, comprising:
   at least one non-transitory computer readable storage device storing information comprising:
   stored computer instructions defining operations to be performed by an imputation engine comprising at least one processor,
   a stored input genetic data set comprising multi-omic genetic expression data including DNA and RNA genetic test results, and
   stored data defining a disease-specific long short-term memory (LSTM) autoencoder configured to impute missing and low-abundance multi-omic genetic markers;
   storage access circuitry operatively coupled to the at least one non-transitory computer readable storage device, the storage access circuitry structured to read:
   the stored input genetic data set comprising the multi-omic genetic expression data including the DNA and RNA genetic test results, and
   the stored data defining the disease-specific LSTM autoencoder; and
   the imputation engine comprising the at least one processor operatively coupled to the storage access circuitry, the at least one processor configured to execute the stored computer instructions to perform operations comprising:
   (a) apply the disease-specific LSTM autoencoder defined by the stored data to the stored input genetic data set comprising the multi-omic genetic expression data including the DNA and RNA test results to impute missing and low-abundance multi-omic genetic markers associated with a specific disease and create a resulting genetic data set including the imputed genetic markers associated with the specific disease, and (b) determine when the stored input genetic data set comprising the multi-omic genetic expression data including the DNA and RNA genetic test results provides insufficient input information to provide confidence of imputation relative to a predictive accuracy threshold and in response thereto, to request additional or deeper sequencing as a basis for reliable imputation, wherein the storage access circuitry is configured to store the resulting genetic data set including the imputed genetic markers associated with the specific disease.

2. The system of claim 1, wherein the at least one processor is further configured by the stored computer instructions to select one or more imputation rules from a database based in part upon at least one of a collected diagnosis, a collected treatment, a collected patient demographic, and/or a collected genetic datum that is part of the input genetic data set, and apply the selected one or more imputation rules to adjust the input genetic data set for imputation by the LSTM autoencoder.

3. The system of claim 2, wherein the at least one processor is further configured by the stored computer instructions to select between plural LSTM autoencoders and applying the selected LSTM autoencoder to the stored input genetic data set.

4. The system of claim 1, wherein the at least one processor is further configured by the stored computer instructions to alter the input genetic data set in response to execution of one or more imputation rules before application of the LSTM autoencoder.

5. The system of claim 4, wherein the resulting genetic data set comprises the input genetic data set and added multi-omic genetic expression data.

6. The system of claim 4, wherein the resulting genetic data set comprises the input genetic data set and at least one changed expression level of the multi-omic genetic expression data.

7. The system of claim 4, wherein the at least one processor is further configured by the stored computer instructions to remove imputed markers from the resulting genetic data set.

8. The system of claim 1, wherein the at least one processor is further configured by the stored computer instructions to perform a Boolean inclusion decision.

9. The system of claim 8, where the at least one processor is further configured by the stored computer instructions to conditionally execute an imputation action specified in one or more imputation rules in response to the Boolean inclusion decision.

10. The system of claim 1 wherein the at least one processor is configured by the stored computer instructions to execute a neural network employing configurable coefficient storage in the form of a coefficient database to populate the neural network with coefficients comprising parameters including weights.

11. The system of claim 1 wherein the at least one processor is further configured by the stored computer instructions to identify mapping of strengths of measured genetic values to imputed markers.

12. The system of claim 1 wherein the disease-specific LSTM autoencoder imputes genetic markers associated with an identified disease having p-values greater than a predetermined stored threshold value.

13. The system of claim 1 wherein the disease-specific LSTM autoencoder is tuned to perform imputation on regions of interest that are prioritized by relevance to a particular disease.

14. A method for variably imputing genetic information into a genetic data set, comprising using at least one processor connected to a non-transitory storage device to execute instructions that control the at least one processor to perform operations comprising:

reading an input genetic data set comprising multi-omic genetic expression data including DNA and RNA genetic test results, determining when the input genetic data set comprising the multi-omic genetic expression data including the DNA and RNA genetic test results provides insufficient input information to provide confidence of imputation of genetic markers relative to a predictive accuracy threshold and in response thereto, obtaining additional or deeper sequencing within the input genetic data set, and applying a disease-specific long short-term memory (LSTM) autoencoder to the input genetic data set comprising the multi-omic genetic expression data including the DNA and RNA genetic test results, the LSTM autoencoder imputing missing and low-expressed multi-omic genetic markers associated with a specific disease, to thereby correct and/or augment the multi-omic genetic expression data including the DNA and RNA genetic test results, classifying the input genetic data set including the imputed missing and low-expressed multi-omic genetic markers with respect to a specific disease, and outputting results of the classifying.

15. The method of claim 14, further comprising selecting one or more imputation rules based in part upon a collected diagnosis and/or a collected genetic datum in the input genetic data set for performing rule-based imputation on the input genetic data set before applying the LSTM autoencoder.

16. The method of claim 14, further comprising selecting data to impute into the input genetic data set based at least in part upon a collected diagnosis and/or collected genetic data present in the input genetic data set.

17. The method of claim 14, wherein the imputed missing and low-expressed multi-omic genetic markers comprises at least one alteration.

18. The method of claim 17, wherein the imputed missing and low-expressed multi-omic genetic markers comprise added genetic expression data.

19. The method of claim 17, wherein the imputed missing and low-expressed multi-omic genetic markers comprise at least one changed expression level of the multi-omic genetic expression data.

20. The method of claim 14, further compromising selectively removing imputed markers from the corrected and/or augmented input multi-omic genetic data set.

21. The method of claim 14, further comprising determining a Boolean inclusion decision for imputation.

22. The method of claim 21, further comprising executing an imputation action specified by one or more imputation rules in response to the Boolean inclusion decision before applying the LSTM autoencoder.

23. The method of claim 14 wherein applying the LSTM autoencoder includes executing, with the at least one processor, a neural network employing configurable coefficient storage in the form of a coefficient database and populating the neural network with coefficients comprising parameters including weights defined based on determined prediction accuracy.

24. A non-transitory computer readable storage device storing instructions that when executed by at least one processor, configure the processor to perform a method for variably imputing genetic information into a collected genetic data set, the instructions comprising:
 first instructions configured for controlling the at least one processor to read the collected genetic data set comprising multi-omic genetic expression data including DNA and RNA genetic test results,
 second instructions configured for controlling the at least one processor to read one or more imputation rules from a database,
 third instructions configured for applying the one or more imputation rules to the collected genetic data set to impute missing and low-expressed genetic markers,
 fourth instructions configured to control the at least one processor to determine when the stored collected genetic data set provides insufficient input information to provide confidence relative to a predictive accuracy threshold and in response thereto, to request additional or deeper sequencing, and
 fifth instructions configured to control the at least one processor to apply to the collected genetic data set and the imputed missing and low-expressed genetic markers, a disease-specific long short-term memory (LSTM) autoencoder tuned to perform imputation of further genetic markers on regions of interest that are prioritized by relevance to a selected disease.

25. The non-transitory computer readable storage device of claim 24 wherein the fifth instructions are configured to control the at least one processor to execute a neural network employing configurable coefficient storage in the form of a coefficient database to populate the neural network with coefficients comprising parameters including weights defined based on determined predictive outcome accuracy.

* * * * *